United States Patent
Konno et al.

(10) Patent No.: US 9,903,710 B2
(45) Date of Patent: Feb. 27, 2018

(54) SHAPE INSPECTION APPARATUS FOR METALLIC BODY AND SHAPE INSPECTION METHOD FOR METALLIC BODY

(71) Applicant: NIPPON STEEL & SUMITOMO METAL CORPORATION, Tokyo (JP)

(72) Inventors: Yusuke Konno, Tokyo (JP); Toshio Akagi, Tokyo (JP); Hironao Yamaji, Tokyo (JP); Jun Umemura, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 0 days.

(21) Appl. No.: 15/514,368

(22) PCT Filed: Jun. 1, 2016

(86) PCT No.: PCT/JP2016/066159
§ 371 (c)(1),
(2) Date: Mar. 24, 2017

(87) PCT Pub. No.: WO2016/194939
PCT Pub. Date: Dec. 8, 2016

(65) Prior Publication Data
US 2017/0276476 A1 Sep. 28, 2017

(30) Foreign Application Priority Data
Jun. 5, 2015 (JP) .................................. 2015-114539

(51) Int. Cl.
*G01B 11/00* (2006.01)
*G01B 11/24* (2006.01)
(Continued)

(52) U.S. Cl.
CPC ................ *G01B 11/24* (2013.01); *G01C 9/02* (2013.01); *H04N 5/2256* (2013.01); *H04N 9/07* (2013.01)

(58) Field of Classification Search
CPC ............................. H04N 5/2256; G01B 11/24
(Continued)

(56) References Cited

U.S. PATENT DOCUMENTS

| 6,757,065 B1 | 6/2004 | Johansson et al. |
| 2002/0039187 A1* | 4/2002 | Keranen ............ G01B 11/2522 356/604 |
| 2014/0043472 A1 | 2/2014 | Takahashi et al. |

FOREIGN PATENT DOCUMENTS

| CN | 102830123 A | 12/2012 |
| JP | 2002-535668 A | 10/2002 |

(Continued)

OTHER PUBLICATIONS

Arguments made in the Japanese Office Action dated Feb. 2, 2017, issued in JP 2016-562275 with English translation.
(Continued)

*Primary Examiner* — Jeffery Williams
(74) *Attorney, Agent, or Firm* — Birch, Stewart, Kolasch & Birch, LLP

(57) ABSTRACT

To inspect the shape of a metallic body further accurately, regardless of surface roughness of the metallic body. A shape inspection apparatus for a metallic body according to the present invention includes: a measurement apparatus configured to irradiate a metallic body with at least two illumination light beams, and measure reflected light of the two illumination light beams from the metallic body separately; and an arithmetic processing apparatus configured to calculate information used for shape inspection of the metallic body on the basis of luminance values of the reflected light. The measurement apparatus includes a first illumination light source and a second illumination light source configured to irradiate the metallic body with strip-shaped illumination light having mutually different peak wavelengths, and a color line sensor camera configured to measure reflected (Continued)

light of first illumination light and reflected light of second illumination light, separately. The first illumination light source and the second illumination light source are provided in a manner that their optical axes form substantially equal angles with a direction of regular reflection of an optical axis of the color line sensor camera at a surface of the metallic body. A wavelength difference between a peak wavelength of the first illumination light and a peak wavelength of the second illumination light is equal to or more than 5 nm and equal to or less than 90 nm.

18 Claims, 26 Drawing Sheets

(51) Int. Cl.
    *G01C 9/02*         (2006.01)
    *H04N 9/07*         (2006.01)
    *H04N 5/225*      (2006.01)

(58) Field of Classification Search
    USPC ........................................................ 348/135
    See application file for complete search history.

(56) References Cited

FOREIGN PATENT DOCUMENTS

| JP | 2003-269931 A | 9/2003 |
|---|---|---|
| JP | 2004-003930 A | 1/2004 |
| JP | 2006-208187 A | 8/2006 |
| JP | 2009-168582 A | 7/2009 |
| JP | 2012-225795 A | 11/2012 |

OTHER PUBLICATIONS

Takaaki Fukui, Color Image Processing in Digital Cameras, 2004, pp. 556-561 with partial English translation.
International Search Report for PCT/JP2016/066159 (PCT/ISA/210) dated Aug. 9, 2016.
Office Action for JP 2016-262275 dated Dec. 6, 2016.
P. Beckmann et al., "The Scattering of Electromagnetic Waves from Rough Surfaces", Artech House Radar Library, 1987, 13 pgs.
Written Opinion of the International Searching Authority for PCT/JP2016/066159 (PCT/ISA/237) dated Aug. 9, 2016.

* cited by examiner

FIG.35

| DIFFERENCE IMAGE | STANDARD DEVIATION OF LUMINANCE VALUES | ANGLE ERROR [deg] |
|---|---|---|
| R – B (R : 640 nm) (B : 460 nm) | 3.50 | 1.6 |
| R – G (R : 640 nm) (G : 530 nm) | 3.09 | 1.4 |
| G – B (G : 530 nm) (B : 460 nm) | 2.06 | 0.9 |

… tion light source capable of emitting third illumination light having a peak wavelength that differs from the peak wavelengths of the first illumination light and the second illumination light by 5 nm or more, the color line sensor camera may further measure reflected light from the metallic body of the third illumination light, and the arithmetic processing apparatus may calculate the inclination of the surface of the metallic body by using the difference and a luminance value of the reflected light of the third illumination light.

The peak wavelength of the first illumination light may be 450 nm or more, and the peak wavelength of the second illumination light may be 540 nm or less.

The peak wavelength of the third illumination light may be equal to or more than 600 nm and equal to or less than 700 nm.

The difference is preferably corrected in advance in a manner that when a metallic body with a flat surface is measured, a difference in luminance value between the two reflected light beams from the metallic body with a flat surface is zero, and the arithmetic processing apparatus preferably specifies a direction of the inclination on the basis of a sign of the difference and specifies a magnitude of the inclination on the basis of an absolute value of the difference.

The arithmetic processing apparatus may further calculate a height of the surface of the metallic body as the information by integrating the calculated inclination of the surface of the metallic body along a relative movement direction of the color line sensor camera and the metallic body.

The arithmetic processing apparatus may inspect a shape of the metallic body by comparing the calculated inclination of the surface of the metallic body with a predetermined threshold value.

According to another aspect of the present invention in order to achieve the above-mentioned object, there is provided a shape inspection method for a metallic body, including: irradiating a metallic body with at least first illumination light and second illumination light, and measuring reflected light of the illumination light from the metallic body separately, by a measurement apparatus including a first illumination light source and a second illumination light source configured to irradiate the metallic body with strip-shaped illumination light having mutually different peak wavelengths, and a color line sensor camera configured to measure reflected light of the first illumination light emitted from the first illumination light source and reflected light of the second illumination light emitted from the second illumination light source, separately, in which the first illumination light source and the second illumination light source are provided in a manner that an angle formed by a direction of regular reflection of an optical axis of the color line sensor camera at a surface of the metallic body and an optical axis of the first illumination light source is substantially equal to an angle formed by the regular reflection direction and an optical axis of the second illumination light source, and a wavelength difference between a peak wavelength of the first illumination light and a peak wavelength of the second illumination light is equal to or more than 5 nm and equal to or less than 90 nm; and calculating, by an arithmetic processing apparatus configured to calculate information for shape inspection of the metallic body on the basis of measurement results of luminance values of the reflected light obtained by the measurement apparatus, an inclination of the surface of the metallic body as the information by using a difference between a luminance value of the reflected light of the first illumination light and a luminance value of the reflected light of the second illumination light.

A surface temperature of the metallic body may be 570° C. or lower.

An angle formed by the optical axis of the color line sensor camera and a normal direction to the surface of the metallic body is preferably set to 5 degrees or less, and the angle formed by the regular reflection direction and the optical axis of the first illumination light source and the angle formed by the regular reflection direction and the optical axis of the second illumination light source are each preferably set to 30 degrees or more.

The measurement apparatus may further include, in the vicinity of the regular reflection direction, a third illumination light source capable of emitting third illumination light having a peak wavelength that differs from the peak wavelengths of the first illumination light and the second illumination light by 5 nm or more, and the color line sensor camera may further measure reflected light from the metallic body of the third illumination light, and in a process of calculating the inclination of the surface in the arithmetic processing apparatus, the inclination of the surface of the metallic body may be calculated by using the difference and a luminance value of the reflected light of the third illumination light.

The peak wavelength of the first illumination light may be set to 450 nm or more, and the peak wavelength of the second illumination light may be set to 540 nm or less.

The peak wavelength of the third illumination light may be set to equal to or more than 600 nm and equal to or less than 700 nm.

The difference is preferably corrected in advance in a manner that when a metallic body with a flat surface is measured, a difference in luminance value between the two reflected light beams from the metallic body with a flat surface is zero, and in a process of calculating the inclination of the surface in the arithmetic processing apparatus, a direction of the inclination is preferably specified on the basis of a sign of the difference and a magnitude of the inclination is preferably specified on the basis of an absolute value of the difference.

In the shape inspection method for a metallic body, by the arithmetic processing apparatus, a height of the surface of the metallic body may be further calculated as the information by integrating the calculated inclination of the surface of the metallic body along a relative movement direction of the color line sensor camera and the metallic body.

In the shape inspection method for a metallic body, a shape of the metallic body may be inspected by comparing the calculated inclination of the surface of the metallic body with a predetermined threshold value.

Advantageous Effects of Invention

According to the present invention, the shape of a metallic body can be inspected accurately at higher speed with higher density, regardless of surface roughness of the metallic body.

BRIEF DESCRIPTION OF DRAWINGS

FIG. 35 is an explanatory diagram for explaining Example 1.

DESCRIPTION OF EMBODIMENTS

Hereinafter. (a) preferred embodiment(s) of the present invention will be described in detail with reference to the appended drawings. In this specification and the drawings, elements that have substantially the same function and structure are denoted with the same reference signs, and repeated explanation is omitted.

(Configuration of Shape Inspection Apparatus)

Figure 1:
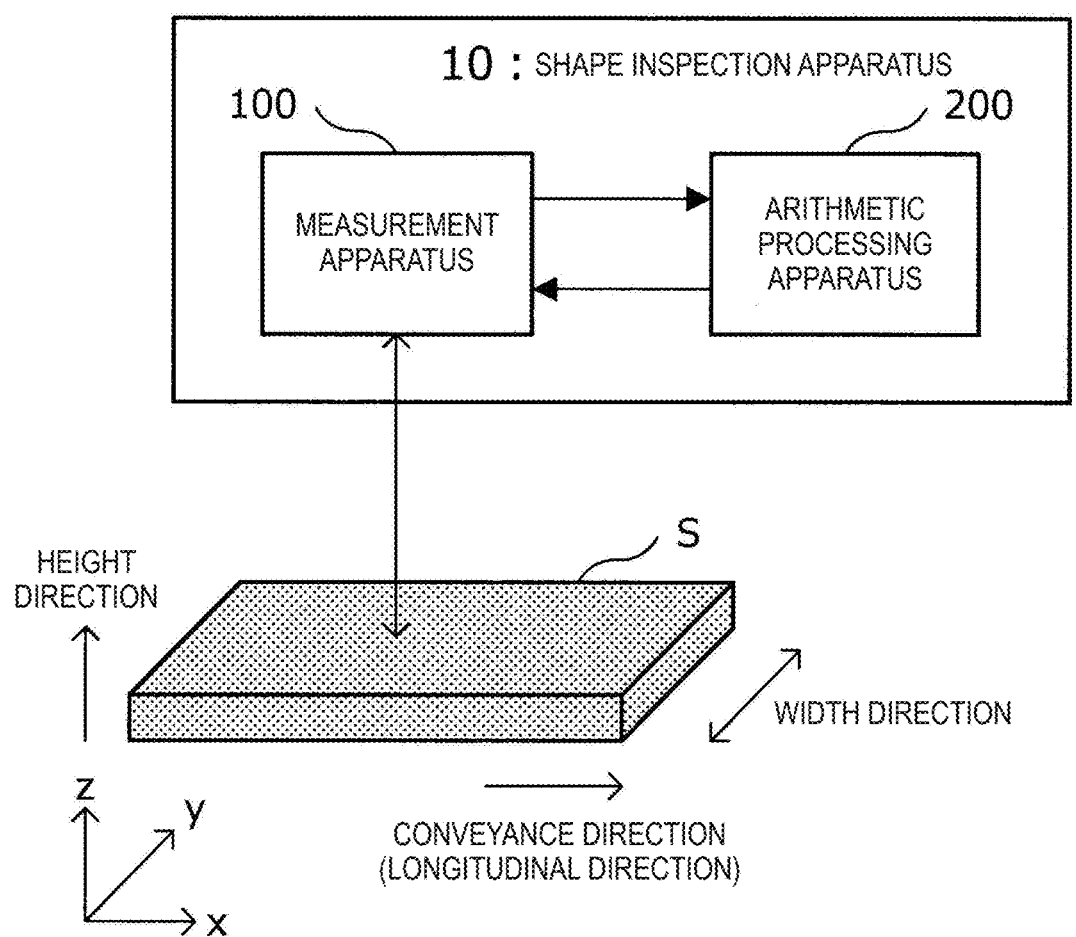
FIG. 1 is an explanatory diagram schematically illustrating an example of a shape inspection apparatus according to an embodiment of the present invention.

First, an overall configuration of a shape inspection apparatus for a metallic body (hereinafter, also simply called a "shape inspection apparatus") 10 according to an embodiment of the present invention will be described with reference to FIG. 1. FIG. 1 is an explanatory diagram illustrating a configuration example of the shape inspection apparatus 10 according to the present embodiment.

The shape inspection apparatus 10 according to the present embodiment is an apparatus that inspects the shapes (e.g., surface shapes) of various metallic bodies S, such as a steel plate placed at a predetermined location and a steel plate conveyed on a predetermined conveyor line.

Here, the shape inspection apparatus 10 and the metallic body move relative to each other; as described above, the shape inspection apparatus 10 may be configured in a manner that a measurement apparatus 100 of the shape inspection apparatus 10 is fixed with respect to the conveyor line and the metallic body is conveyed on the conveyor line, or in a manner that the measurement apparatus 100 moves with respect to a still metallic body.

A macroscopic shape of the metallic body S is not particularly limited and may be, for example, a plate shape (e.g., a slab or a billet) or a strip shape.

Components of the metallic body S are also not particularly limited, and the metallic body S may be various types of steel containing an iron element as the main component, various types of alloy of iron and other metal elements, or various types of nonferrous metal.

The metallic body S is ordinarily subjected to a hot rolling step and then to a pickling step and a cold rolling step, and undergoes a plating step and the like to be a product. In a red-hot state of 570° C. or higher in the hot rolling step, heat radiation of the metallic body S itself may serve as a factor of errors of image capturing in the measurement apparatus 100 described later.

In general, a steel plate that has been subjected to a hot rolling process has an oxide film called scale generated on its surface; thus, the steel plate has small irregularity in surface roughness, but the interface between the oxide film and base metal iron is ununiform rather than flat. Therefore, in a pickling step of removing the scale, the surface of the base metal iron appears as a rough surface. In addition, surface roughness is intentionally imparted to a product in a cold rolling process; thus, a steel plate after cold rolling has large irregularity in surface roughness. Therefore, in the case where the technology disclosed in Patent Literature 3 is used for the steel plate after cold rolling, it is difficult to measure the surface shape accurately. However, the shape inspection apparatus 10 according to the present embodiment, which is described below, can perform inspection of the surface shape precisely, even when the metallic body S has large irregularity in surface roughness, like a steel plate that has been subjected to a cold rolling process.

In the following description, the metallic body S is assumed to be conveyed along the longitudinal direction of the metallic body S on a conveyor line (not illustrated), and the longitudinal direction of the metallic body S is also called a conveyance direction.

This shape inspection apparatus 10 mainly includes the measurement apparatus 100 and an arithmetic processing apparatus 200, as illustrated in FIG. 1.

Under control of the arithmetic processing apparatus 200, the measurement apparatus 100 irradiates the metallic body S (specifically, the surface of the metallic body S) with at least two types of illumination light, and measures reflected light from the metallic body S (specifically, the surface of the metallic body S) of the illumination light separately to generate data on luminance values of the reflected light. The measurement apparatus 100 outputs the generated data on the luminance values of the reflected light to the arithmetic processing apparatus 200.

The arithmetic processing apparatus 200 controls a measurement process of the metallic body S by the measurement apparatus 100. In addition, the arithmetic processing apparatus 200 acquires the data on the luminance values of the reflected light, generated by the measurement apparatus 100, and performs data processing, which will be described in detail later, on the acquired data on the luminance values, thereby calculating various types of information used for inspecting the shape (specifically, surface shape) of the metallic body S. In the following description, various types of information used for shape inspection is collectively called "information for inspection". Examples of the information for inspection calculated by the arithmetic processing apparatus 200 include, as will be described in detail later, information on an inclination of the surface of the metallic body S, which is calculated on the basis of a difference between luminance values of reflected light of two types of illumination light, and information on a height of the surface of the metallic body S, which is obtained by integrating the inclination of the surface. In other words, the information on an inclination of the surface of the metallic body S and the information on a height of the surface serve as information indicating the shape of the metallic body S.

The measurement process of the metallic body S by the measurement apparatus 100 and a calculation process of information for inspection by the arithmetic processing apparatus 200 can be performed in real time along with conveyance of the metallic body S. A user of the shape inspection apparatus 10 can recognize in real time the shape of the metallic body S and inspect the metallic body S by focusing on inspection results output from the shape inspection apparatus 10 (specifically, the arithmetic processing apparatus 200).

Hereinafter, each of the measurement apparatus 100 and the arithmetic processing apparatus 200 will be described in detail.

<Measurement Apparatus 100>

First, the measurement apparatus 100 according to the present embodiment will be described in detail with reference to FIGS. 2A to 23.

Figure 19:
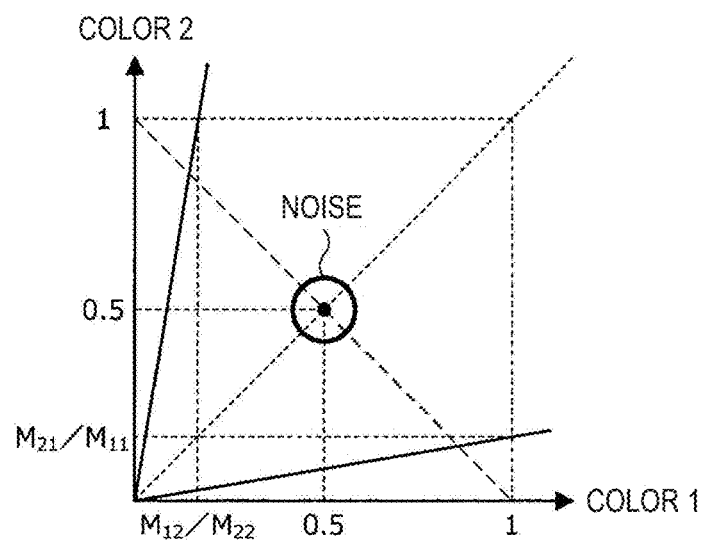
FIG. 19 is an explanatory diagram for explaining wavelengths of illumination light in a measurement apparatus according to the embodiment.
Figure 20:
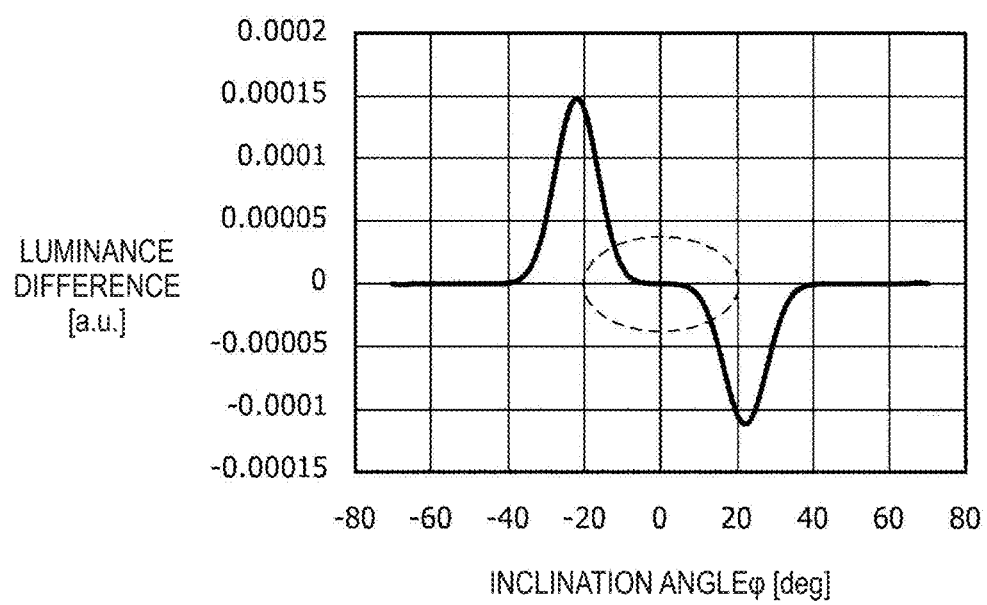
FIG. 20 is a graph diagram showing an example of the relation between a luminance difference of reflected light of first and second illumination light and an inclination angle of a metallic body surface.
Figure 21:
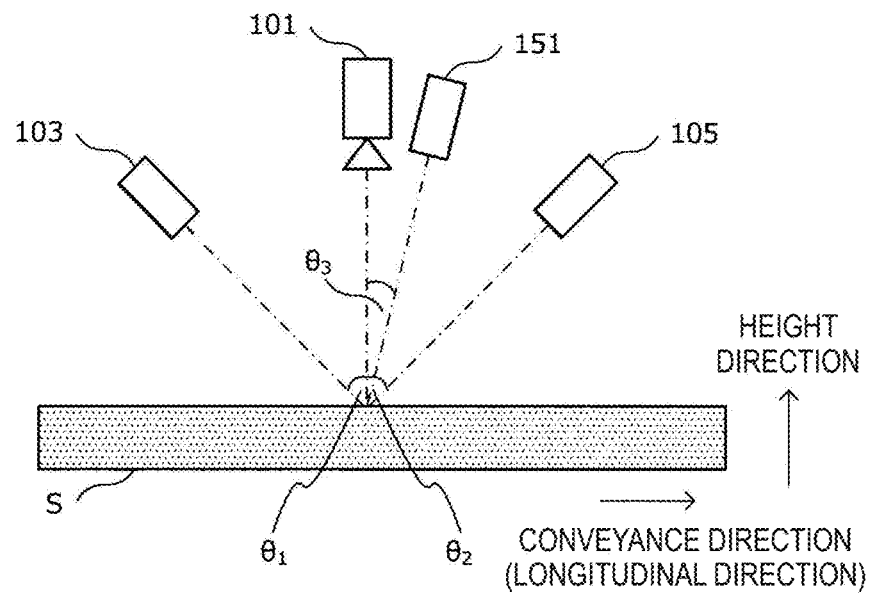
FIG. 21 is an explanatory diagram schematically illustrating another example of a measurement apparatus included in a shape inspection apparatus according to the embodiment.
Figure 22:
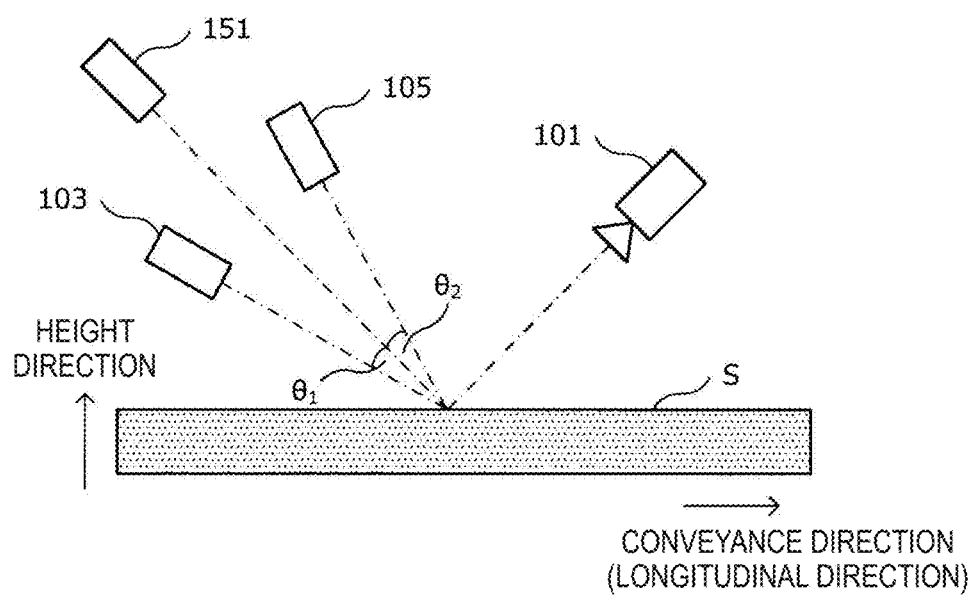
FIG. 22 is an explanatory diagram schematically illustrating another example of a measurement apparatus included in a shape inspection apparatus according to the embodiment.
Figure 23:
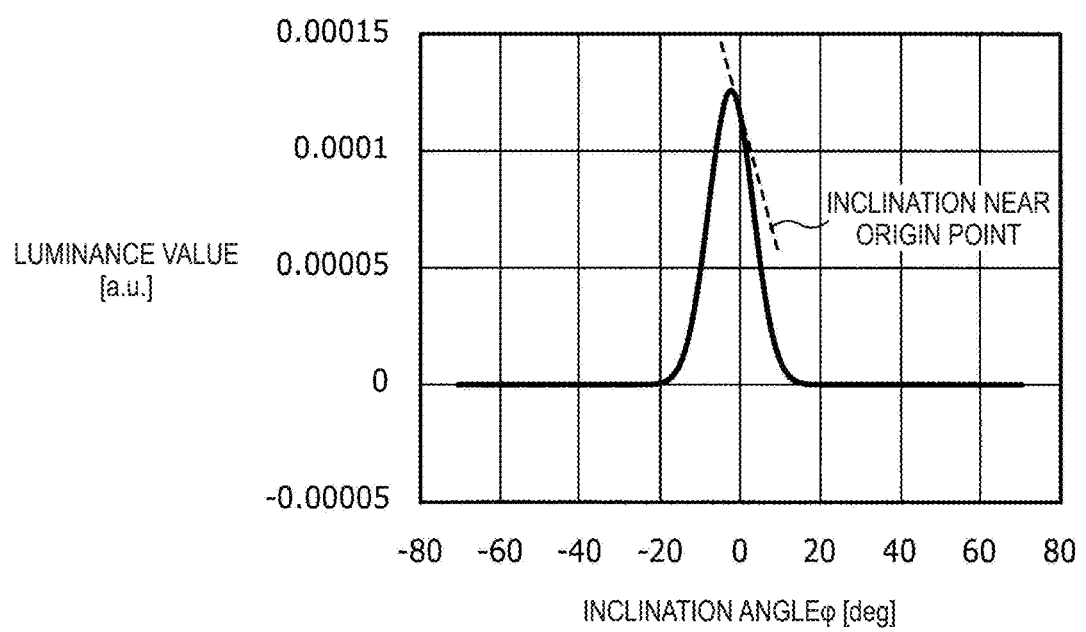
FIG. 23 is an explanatory diagram showing an example of the relation between a luminance value of reflected light of third illumination light and an inclination angle of a metallic body surface.

FIGS. 2A to 4 are explanatory diagrams schematically illustrating an example of a measurement apparatus included in the shape inspection apparatus 10 according to the present embodiment. FIGS. 5 to 8 and FIGS. 10 to 19 are explanatory diagrams for explaining wavelengths of illumination light in the measurement apparatus 100 according to the present embodiment. FIG. 9 is an explanatory diagram schematically illustrating the relation between a reflection angle of illumination light and an inclination angle of a surface in the measurement apparatus according to the present embodiment. FIG. 20 is a graph diagram showing an example of the relation between a luminance difference of reflected light of first and second illumination light and an inclination angle of a metallic body surface. FIGS. 21 and 22 are explanatory diagrams each schematically illustrating another example of a measurement apparatus included in the shape inspection apparatus according to the present embodiment. FIG. 23 is an explanatory diagram showing an example of the relation between a luminance value of reflected light of third illumination light and an inclination angle of a metallic body surface.

Figure 2A:
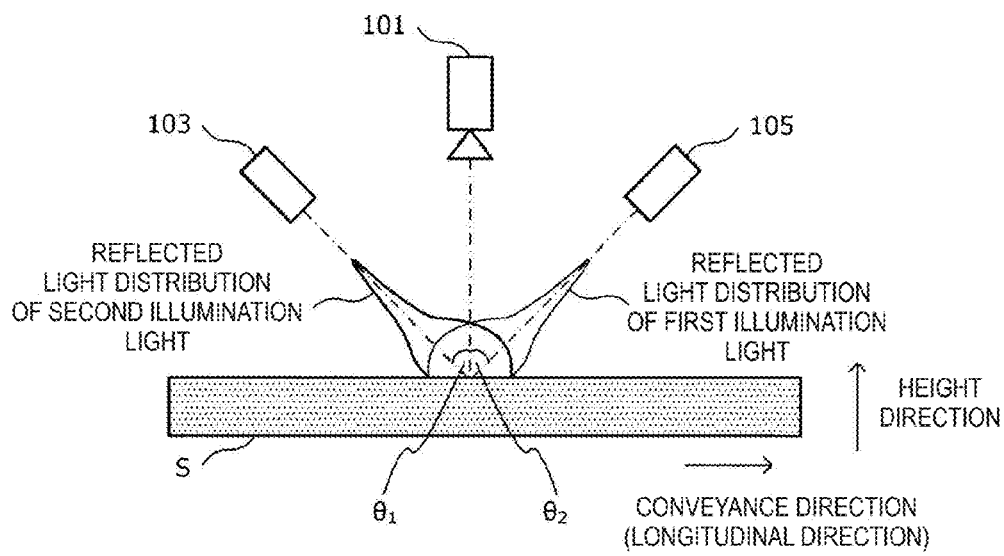
FIG. 2A is an explanatory diagram schematically illustrating an example of a measurement apparatus included in a shape inspection apparatus according to the embodiment.
Figure 2B:
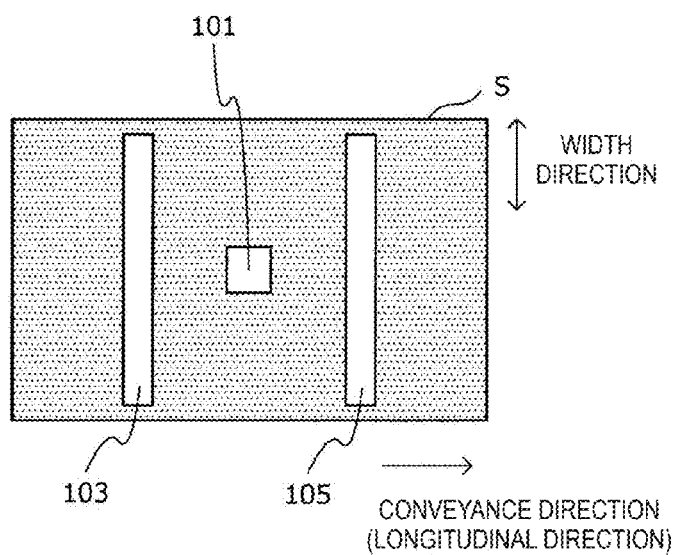
FIG. 2B is an explanatory diagram schematically illustrating an example of a measurement apparatus included in a shape inspection apparatus according to the embodiment.
Figure 2C:
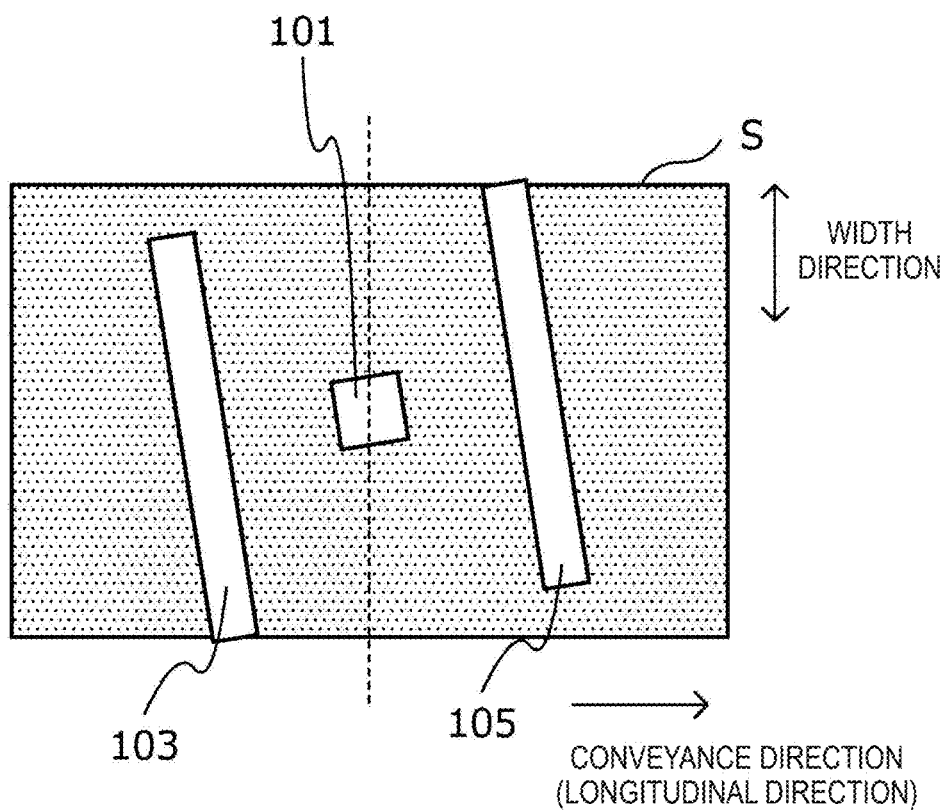
FIG. 2C is an explanatory diagram schematically illustrating an example of a measurement apparatus included in a shape inspection apparatus according to the embodiment.

FIG. 2A is a schematic diagram viewing the measurement apparatus 100 from the side of the metallic body S. FIGS. 2B and 2C are schematic diagrams viewing the measurement apparatus 100 from above the metallic body S.

As illustrated in FIGS. 2A and 2B, the measurement apparatus 100 according to the present embodiment includes at least a color line sensor camera 101, a first illumination light source 103, and a second illumination light source 105. The color line sensor camera 101, the first illumination light source 103, and the second illumination light source 105 are fixed by known means so that their set positions do not change.

In FIG. 2A, the color line sensor camera 101 is provided above the metallic body S (the positive direction side of the z-axis) in a manner that its optical axis is perpendicular to the surface of the metallic body S (hereinafter, also called a "metallic body surface"). Note that "perpendicular to the metallic body surface" means that the optical axis of the color line sensor camera 101 and the tangent plane of the metallic body S at the intersection point of the optical axis and the metallic body surface form a perpendicular angle. The color line sensor camera 101 measures reflected light at the metallic body surface of first illumination light emitted from the first illumination light source 103 and second illumination light emitted from the second illumination light source 105, separately. Thus, the color line sensor camera 101 can specify data indicating intensity of the reflected light at the metallic body surface of the first illumination light and the second illumination light (i.e., data indicating luminance values of the reflected light). Image capturing is performed with the color line sensor camera 101 each time the metallic body S is conveyed a constant distance, for example, and consequently the color line sensor camera 101 can specify distribution of the reflected light at the metallic body surface of the first illumination light in the conveyance direction and the width direction (in the xy plane of FIG. 1) and distribution of the reflected light at the metallic body surface of the second illumination light in the conveyance direction and the width direction (in the xy plane of FIG. 1).

The first illumination light source 103 and the second illumination light source 105 are LEDs or lasers, or light sources each configured to emit light that can be regarded as quasi-monochromatic light obtained by causing a band-pass filter to transmit white light from a white light source, and emit light having mutually different peak wavelengths. The color line sensor camera 101 includes at least two line sensors, and each line sensor is provided with a color filter having a transmitted wavelength band such that transmittance for a peak wavelength of one given illumination light beam is higher than transmittance for a peak wavelength of another illumination light beam. Since each line sensor is provided with such a color filter, the color line sensor camera 101 can measure reflected light of the first illumination light and reflected light of the second illumination light separately.

As the color line sensor camera 101, a known color line sensor camera can be used. Thus, the magnitudes of various wavelength components (e.g., R component, G component, and B component) included in the reflected light of the first illumination light and the second illumination light can be measured independently at the same time.

Here, the R component (red component) indicates a component corresponding to light with a peak wavelength of 600 to 700 nm, for example, the G component (green component) indicates a component corresponding to light with a peak wavelength of 500 to 560 nm, for example, and the B component (blue component) indicates a component corresponding to light with a peak wavelength of 430 nm to 500 nm, for example.

The color line sensor camera 101 measures luminance values of the reflected light of the first illumination light and the second illumination light separately, generates data corresponding to the obtained measurement results (data on luminance values of reflected light), and outputs the data to the arithmetic processing apparatus 200 described later.

The first illumination light source 103 and the second illumination light source 105 irradiate the surface of the metallic body S with the first illumination light and the second illumination light, respectively. The first illumination light and the second illumination light have mutually different peak wavelengths. The emission spectrum distribution of the first illumination light source 103 and the second illumination light source 105 may include an overlap as long as peak wavelengths are different from each other.

Separating the first illumination light and the second illumination light by the method described above, for example, makes it easy to specify whether the distribution of luminance values of reflected light measured by the color line sensor camera 101 corresponds to the first illumination light or the second illumination light.

Here, as the first illumination light source 103 and the second illumination light source 105, any light source can be used as long as it can irradiate substantially the entire area of the metallic body S in the width direction with illumination light as illustrated in FIG. 2B, for example. As this light source, a rod-like LED light can be utilized, and a laser beam expanded by a rod lens or the like into a linear shape can be used as well, for example. Moreover, as a visible light source used as the first illumination light source 103 and the second illumination light source 105, a light source like a single-wavelength laser beam or an LED with a narrow emission wavelength band may be used, or a light source with a continuous spectrum like a xenon lamp may be used in combination with a color filter.

A method for selecting peak wavelengths of the first illumination light source 103 and the second illumination light source 105 is described in detail below.

An angle formed by a regular reflection direction of the color line sensor camera 101 (a normal direction to the metallic body surface in FIG. 2A) and the optical axis of the first illumination light source 103 is denoted by $\theta_1$, and an angle formed by the regular reflection direction and the optical axis of the second illumination light source 105 is denoted by $\theta_2$. In this case, the first illumination light source 103 and the second illumination light source 105 are provided above the metallic body S (the positive direction side of the z-axis) in a manner that $\theta_1$ and $\theta_2$ are substantially equal to each other.

Here, "$\theta_1$ and $\theta_2$ are substantially equal to each other" includes not only a case where $\theta_1$ and $\theta_2$ are equal to each other but also a case where $\theta_1$ and $\theta_2$ have an angle difference in a range such that, when images of a plane without unevenness are captured using the first illumination light source 103 and the second illumination light source 105, the plane without unevenness appears the same, with a change in luminance due to dirt etc. on the plane taken into account. This angle difference $|\theta_1-\theta_2|$ between $\theta_1$ and $\theta_2$ is preferably 10 degrees or less, for example, further preferably 5 degrees or less. An angle difference in such a range allows two captured images to appear the same when images of a plane without unevenness are captured using the respective illumination light beams.

The angles $\theta_1$ and $\theta_2$ are preferably as large as possible, as long as there is no constraint on light source installation. Thus, irregular reflection of respective illumination light beams can be measured by the color line sensor camera 101. For example, $\theta_1$ and $\theta_2$ are both preferably 30 degrees or more. By setting each of $\theta_1$ and $\theta_2$ to 30 degrees or more, a change in luminance value relative to an angle change, measured by the color line sensor camera 101, can be further increased.

Since the color line sensor camera 101, the first illumination light source 103, and the second illumination light source 105 are provided as illustrated in FIGS. 2A and 2B, when a plane without unevenness is measured, reflected light of the first illumination light has a luminance value substantially equal to a luminance value of reflected light of the second illumination light. On the other hand, when the metallic body surface has unevenness, the unevenness causes a change in the inclination of the surface, causing a difference in reflected light intensity of the first and second illumination light in the camera direction; thus, a difference in luminance value occurs between reflected light of the first illumination light and reflected light of the second illumination light.

The first illumination light source 103 and the second illumination light source 105 are installed in a manner that their longitudinal directions are substantially parallel to the width direction of the metallic body S in the example illustrated in FIGS. 2A and 2B. In this case, a difference in luminance value due to an inclination parallel to the conveyance direction (more accurately, an inclination rotated around an axis parallel to the conveyance direction) does not occur. Hence, to detect such an inclination, the first illumination light source 103 and the second illumination light source 105 may be provided in a manner that their longitudinal directions are inclined with respect to the width direction of the metallic body S as illustrated in FIG. 2C. By arranging the illumination light sources with inclination as illustrated in FIG. 2C, even in the case where the surface of the metallic body S has unevenness and an inclination due to the unevenness is parallel to the conveyance direction, the inclination can be detected on the basis of a difference in luminance value between two reflected light beams.

Figure 3:
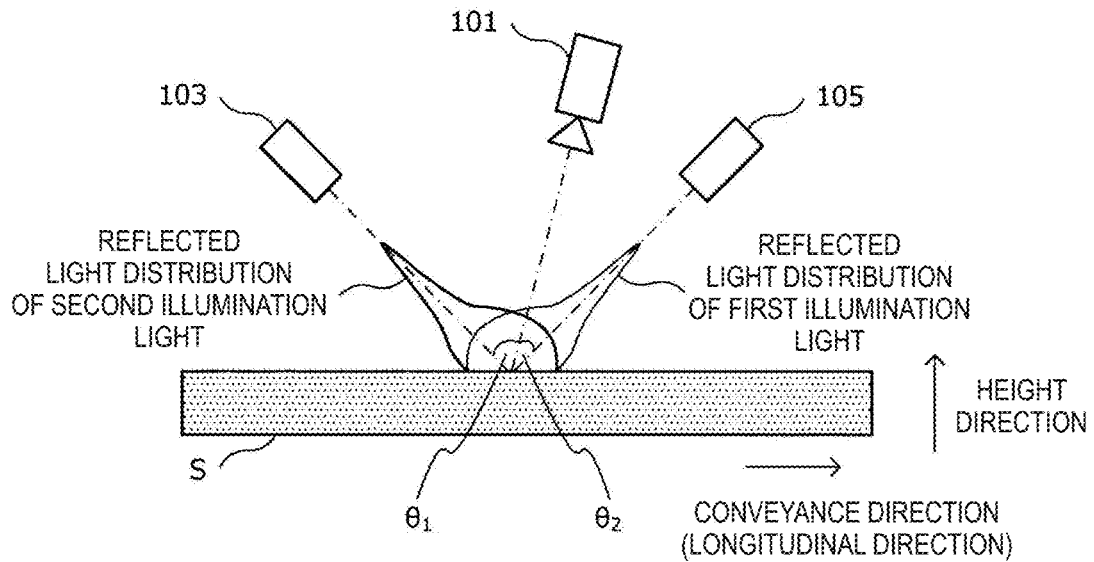
FIG. 3 is an explanatory diagram schematically illustrating an example of a measurement apparatus included in a shape inspection apparatus according to the embodiment.

FIG. 3 is a schematic diagram viewing the measurement apparatus 100 from the side of the metallic body S. The color line sensor camera 101 is provided in a manner that its optical axis is perpendicular to the surface of the metallic body S in the example illustrated in FIG. 2A, but the optical axis of the color line sensor camera 101 may be inclined with respect to the normal direction to the metallic body surface (i.e., the normal direction to the tangent plane of the metallic body at the intersection point of the optical axis of the color line sensor camera 101 and the metallic body surface) as illustrated in FIG. 3. In this case, an angle formed by the optical axis of the color line sensor camera 101 and the normal to the metallic body surface is preferably 5 degrees or less, for example. When the color line sensor camera 101 is installed with an angle difference within this range, with regard to a plane without unevenness, reflected light of the first illumination light has a luminance value substantially equal to a luminance value of reflected light of the second illumination light.

Figure 4:
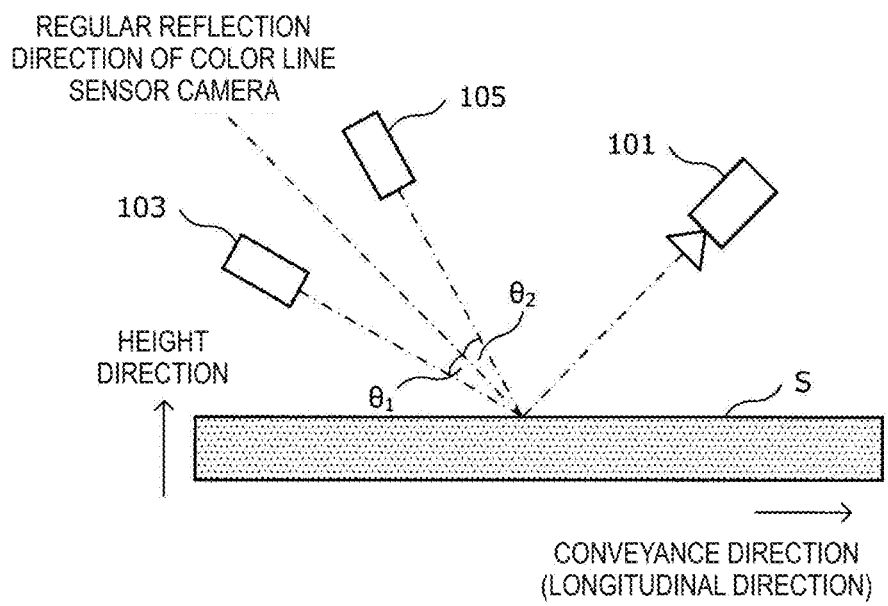
FIG. 4 is an explanatory diagram schematically illustrating an example of a measurement apparatus included in a shape inspection apparatus according to the embodiment.

FIG. 4 is a schematic diagram viewing the measurement apparatus 100 from the side of the metallic body S. The first illumination light source 103 and the second illumination light source 105 are provided in a balanced way at the upstream side and the downstream side in the conveyance direction with respect to the color line sensor camera 101 in FIGS. 2A to 3. However, as illustrated in FIG. 4, it is also possible to arrange the color line sensor camera 101 with great inclination with respect to the surface, and collectively arrange the first illumination light source 103 and the second illumination light source 105 at the upstream side (in the case where the color line sensor camera 101 is installed at the downstream side as illustrated in FIG. 4) or the downstream side (in the case where the color line sensor camera 101 is installed at the upstream side) with respect to the color line sensor camera 101 in a manner that each illumination light source faces the color line sensor camera 101. Also in this case, the angles $\theta_1$ and $\theta_2$ illustrated in the drawing are preferably substantially equal to each other, and each angle is preferably as large as possible.

The configuration of the measurement apparatus 100 according to the present embodiment has been described in detail with reference to FIGS. 2A to 4.

FIGS. 2A to 3 illustrate a case where the first illumination light source 103 is provided at the upstream side in the conveyance direction and the second illumination light source 105 is provided at the downstream side in the conveyance direction, but it is also possible to provide the second illumination light source 105 at the upstream side in the conveyance direction and provide the first illumination light source 103 at the downstream side in the conveyance direction.

[Method for Selecting Wavelengths of Illumination Light]

Now, a method for selecting wavelengths of illumination light in the measurement apparatus 100 according to the present embodiment will be described in detail with reference to FIGS. 5 to 23.

Upper Limit Value of Difference Between Peak Wavelengths of Two Illumination Light Beams Models for simulating reflection of light at a metal rough surface include Kirchhoff-Beckmann-Spizzichino model (hereinafter abbreviated as "KBS model") disclosed in Non-Patent Literature 1. The KBS model expresses reflectance of light at a given surface as a function that is dependent on an incident angle and a reflection angle of light at the surface, surface roughness, and correlation length of the surface shape.

Figure 5:
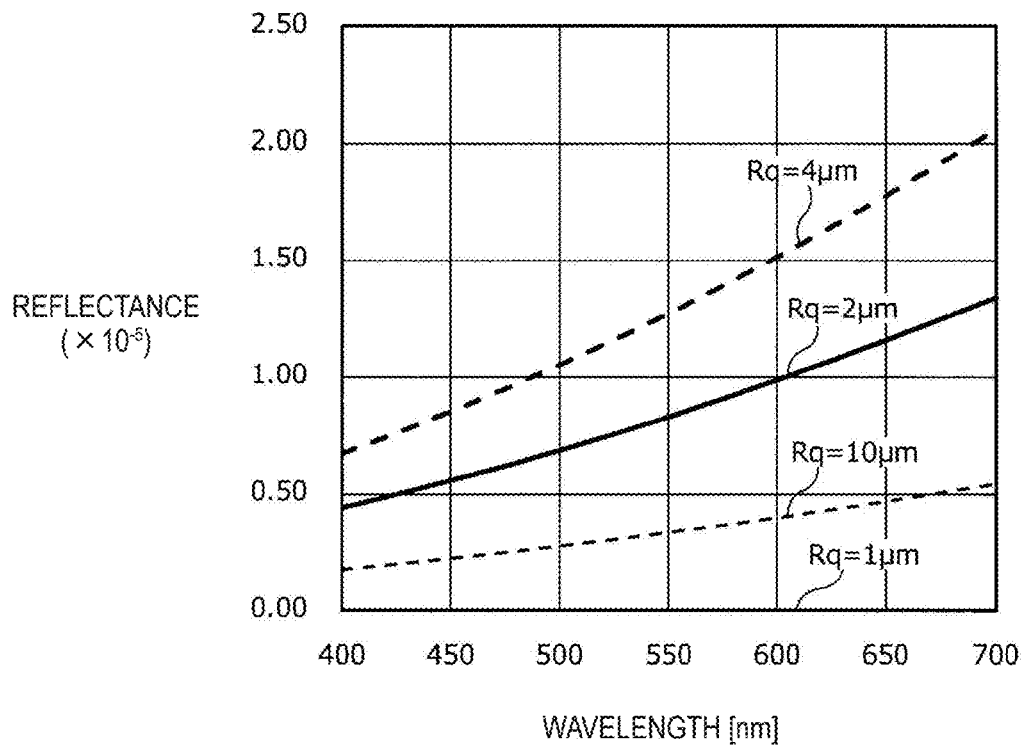
FIG. 5 is an explanatory diagram for explaining wavelengths of illumination light in a measurement apparatus according to the embodiment.

The correlation length of surface roughness of the surface of interest is set to 15 μm, the incident angle is set to 45 degrees, and the reflection angle of reflected light reflected into a plane including incident light and a normal is set to 45 degrees. Surface reflectance in the KBS model in this case is calculated regarding four types of surface roughness and shown in FIG. 5. Here, the surface roughness of interest is of four types of root-mean-square roughness Rq of 1 μm, 2 μm, 1 μm, 4 μm, and 10 μm. In FIG. 5, the vertical axis indicates reflectance, and the horizontal axis indicates a wavelength of light incident on the surface. Note that the result for Rq=1 μm exhibits values extremely close to zero, substantially overlapping with the horizontal axis in FIG. 5.

FIG. 5 reveals that with the angles set above, longer wavelengths of light result in larger reflectance with regard to each surface roughness. Moreover, the obtained reflectance fluctuates according to surface roughness.

In the case where a steel plate is assumed as the metallic body S, for example, fluctuation in surface roughness is caused by irregularity in roughness imparted to a rolling mill roll in cold rolling, a change in the base metal iron interface due to a difference in scale generation in cooling with regard to a steel plate after a pickling step, and irregularity in surface alloying with regard to a plated steel plate. Therefore, in the case where illumination light having two types of wavelengths is used as in the measurement apparatus 100 according to the present embodiment, reflectance fluctuates for each of the used illumination light beams. In the case of a non-mirror-finished metal surface, the steel plate ordinarily has roughness of approximately 1 to 3 μm, and a change in roughness that may occur in ordinary operation is approximately ±10%.

By the way, as will be described in detail later, the arithmetic processing apparatus 200 according to the present embodiment uses luminance values of reflected light of two illumination light beams to calculate a difference between the two luminance values, and calculates an inclination of the surface of the metallic body S using the obtained luminance difference. Here, as described above using the KBS model as an example, when light incident on the surface of the metallic body S has different wavelengths, reflectance at the surface fluctuates according to the wavelength as shown in FIG. 5. Consequently, when luminance values of two reflected light beams are measured by a color line sensor camera with regard to a surface known to be flat and a difference between the obtained luminance values is calculated, the luminance difference, which originally is to be zero, exhibits a value other than zero.

Figure 6:
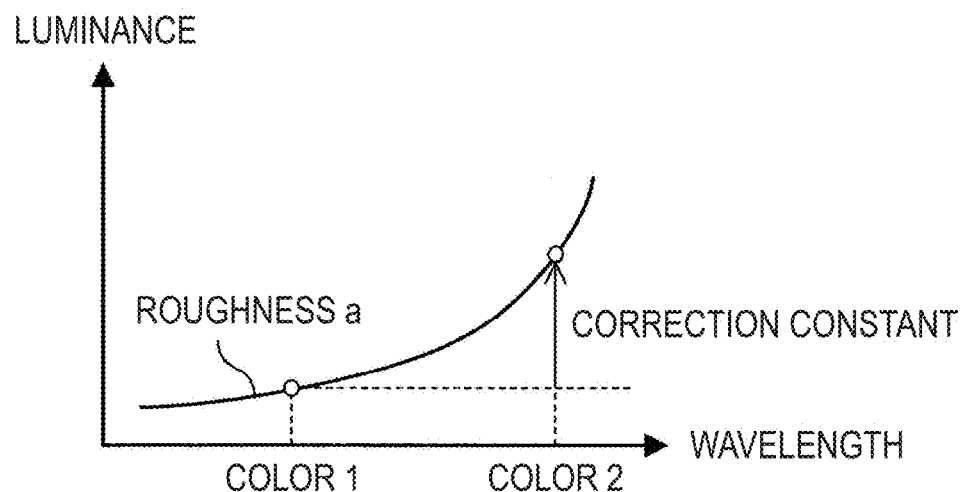
FIG. 6 is an explanatory diagram for explaining wavelengths of illumination light in a measurement apparatus according to the embodiment.

This phenomenon is schematically expressed in FIG. 6. As schematically shown in FIG. 6, in the case where a given surface has surface roughness a (μm), a luminance value of reflected light from the surface changes between color 1 and color 2. As will be described later, in the arithmetic processing apparatus 200 according to the present embodiment, the sign of a luminance difference obtained as a result of arithmetic of (luminance value for color 1)−(luminance value for color 2) is used to determine the direction of the inclination of the surface (i.e., whether the direction is a direction in which inclination increases or a direction in which inclination decreases), and the absolute value of the luminance difference is used to decide the magnitude of the inclination angle, for example. Accordingly, when the situation shown in FIG. 6 causes a value other than zero in arithmetic of a difference that originally is to be zero, this serves as a factor of measurement errors.

Hence, in the arithmetic processing apparatus 200 according to the present embodiment, as will be described in detail later, a correction constant is set experimentally beforehand in a manner that a difference calculation formula expressed by the following formula 101 is zero when a surface known to be flat (i.e., a surface whose inclination is zero) is measured.

luminance difference=(luminance value for color 1)−(luminance value for color 2)+correction constant     (formula 101)

Here, the reflectance curve shown in FIG. 5 varies depending on surface roughness of a measured material; thus, the value of the correction constant in the above formula 101 also varies depending on surface roughness of a measured material. Accordingly, in the case where roughness is imparted intentionally as with a cold-rolled material, it is preferable to find beforehand a value of the correction constant corresponding to surface roughness of a product to be produced, and save the surface roughness and the correction constant in correspondence with each other.

Figure 7:
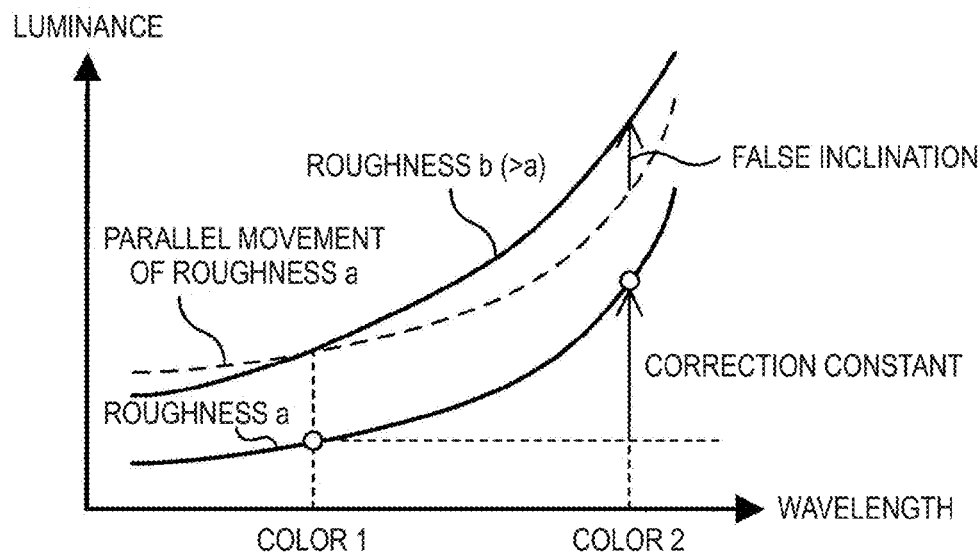
FIG. 7 is an explanatory diagram for explaining wavelengths of illumination light in a measurement apparatus according to the embodiment.

Here, assume a case where surface roughness of the metallic body S fluctuates. If the luminance value changes by the same amount for each wavelength (in other words, if a luminance curve simply moves parallel as shown in FIG. 7), the value of the above formula 101 in which the correction constant is decided appropriately persists at zero. Actually, however, a change in luminance value varies depending on the wavelength as schematically shown in FIG. 7, which causes false inclination. In the example shown in FIG. 7, even in the case where the correction constant for color 2 is decided appropriately regarding the roughness a in advance, when roughness changes to b (>a) during shape inspection, a change in luminance value cannot be corrected sufficiently only with the correction constant decided appropriately in advance, and a luminance difference corresponding to insufficiency of correction is recognized as false inclination.

Accordingly, peak wavelengths of two illumination light beams used in the measurement apparatus 100 according to the present embodiment are preferably values as close as possible to each other. Hence, in the measurement apparatus 100 according to the present embodiment, the upper limit value of a difference between peak wavelengths of two illumination light beams is defined according to the reason described below.

Assume that an illumination light source that emits illumination light with a peak wavelength of 530 nm and an illumination light source that emits illumination light with a peak wavelength of 460 nm are installed with $|\theta_1|$ and $|\theta_2|$ illustrated in FIG. 2A each set to 45 degrees to the color line sensor camera 101. On this occasion, root-mean-square roughness Rq is set to 1.5 μm, correlation length is set to 15 μm, and an incident angle is set to 45 degrees on the basis of the KBS model, and intensity of reflected light that forms an image in the color line sensor camera 101 is calculated and shown in FIG. 8. Here, the horizontal axis in FIG. 8 indicates an inclination angle φ of the surface, and the vertical axis indicates a luminance value of reflected light. As schematically illustrated in FIG. 9, the inclination angle φ of the surface is different from reflection angles $\theta_1$ and $\theta_2$ of illumination light. In this simulation, the settings of surface roughness, root-mean-square roughness Rq of 1.5 μm and correlation length of 15 μm, are appropriate values for a model expressing the surface of a general metallic body S, such as a steel plate.

Figure 8:
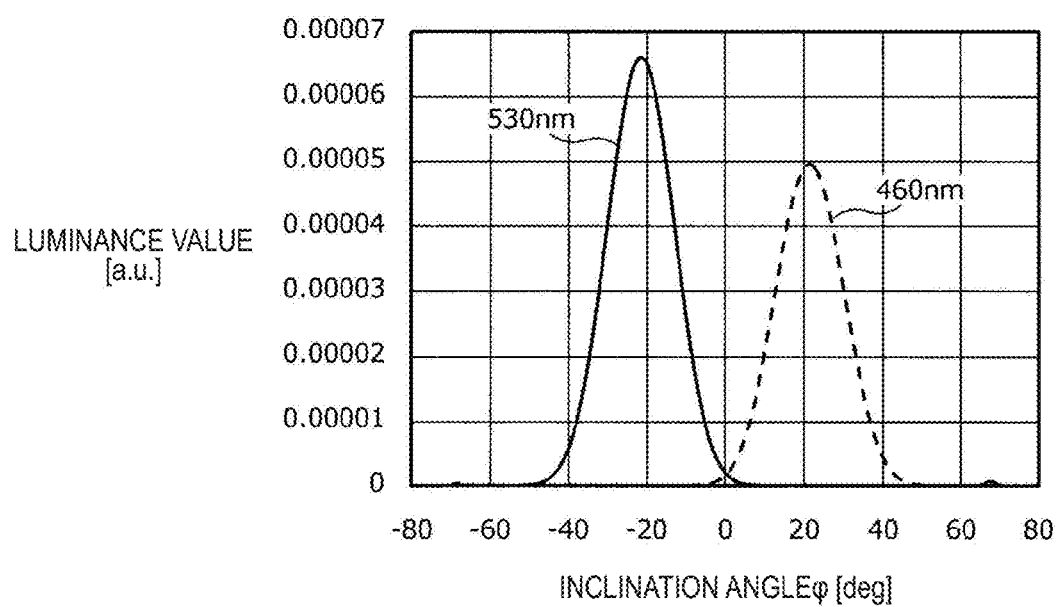
FIG. 8 is an explanatory diagram for explaining wavelengths of illumination light in a measurement apparatus according to the embodiment.
Figure 9:
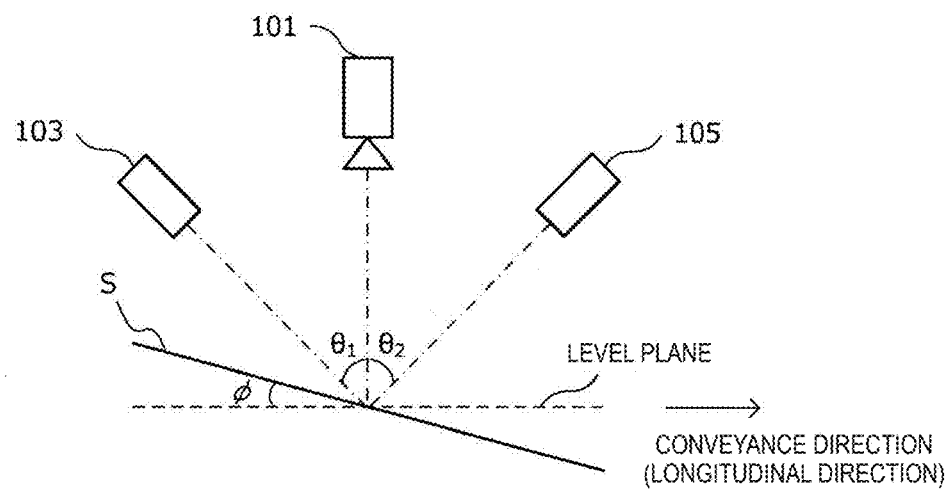
FIG. 9 is an explanatory diagram schematically illustrating the relation between a reflection angle of illumination light and an inclination angle of a surface in a measurement apparatus according to the embodiment.
Figure 10:
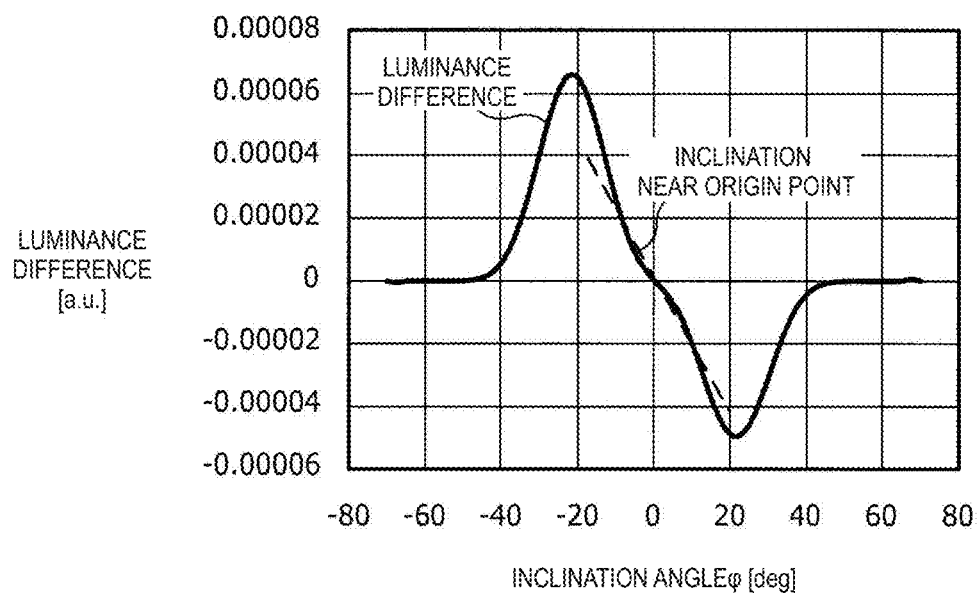
FIG. 10 is an explanatory diagram for explaining wavelengths of illumination light in a measurement apparatus according to the embodiment.

In the arithmetic processing apparatus 200 according to the present embodiment, when measurement data on luminance values of reflected light as shown in FIG. 8 is obtained, luminance difference data as shown in FIG. 10 is generated by using the formula 101 in which the correction constant is decided appropriately. Here, in the luminance difference data shown in FIG. 10, the horizontal axis indicates the inclination angle φ expressing the degree of inclination of the surface of a metallic body of interest, and the vertical axis indicates a luminance difference.

In the measurement apparatus 100 according to the present embodiment, as illustrated in FIG. 2A and the like, the first illumination light source 103 and the second illumination light source 105 are installed (fixed) in a manner that their optical axes form predetermined angles $|\theta_1|\approx|\theta_2|$ with the optical axis of the color line sensor camera 101. This angle will be called a light source angle θ. In the present embodiment, the first illumination light source 103 and the second illumination light source 105 are installed so as to have substantially equal light source angles. Therefore, when images of a plane that is kept level are captured, with regard to measured luminances of reflected light detected by the color line sensor camera 101, a luminance difference between a measured luminance of reflected light of the first illumination light and a measured luminance of reflected light of the second illumination light can be regarded as zero, except for a small difference corresponding to the correction constant due to a difference in wavelength. Here, when an inclination tan φ in the longitudinal direction of the metallic body S occurs in a plane that is kept level, the degrees of reflection of illumination light beams change, causing a change in a luminance difference between reflected light beams.

Luminance difference data shown in FIG. 10 reveals correlation between the inclination angle φ and the luminance difference. Hence, in the arithmetic processing apparatus 200 according to the present embodiment, fluctuation in luminance difference due to a roughness change is converted into an inclination angle, according to the relation between the inclination angle and the luminance difference shown in FIG. 10, for example. Specifically, a conversion coefficient for converting a luminance difference into an angle is decided according to an inclination of the graph near the origin point, i.e., at an inclination angle φ of zero degrees, in FIG. 10. This conversion coefficient is changed also by aperture of lenses provided in the color line sensor camera 101, or the like; hence, the conversion coefficient is decided experimentally in advance by using an optical system used for actual measurement.

In converting a luminance difference into an inclination angle by the arithmetic described above, in the shape inspection apparatus 10 according to the present embodiment, the upper limit value of a difference between peak wavelengths of two illumination light beams is defined in a manner that a calculation error of surface inclination is 1 degree or less with respect to a roughness change of 10%. A method for deciding the upper limit value is described in detail below.

Figure 11:
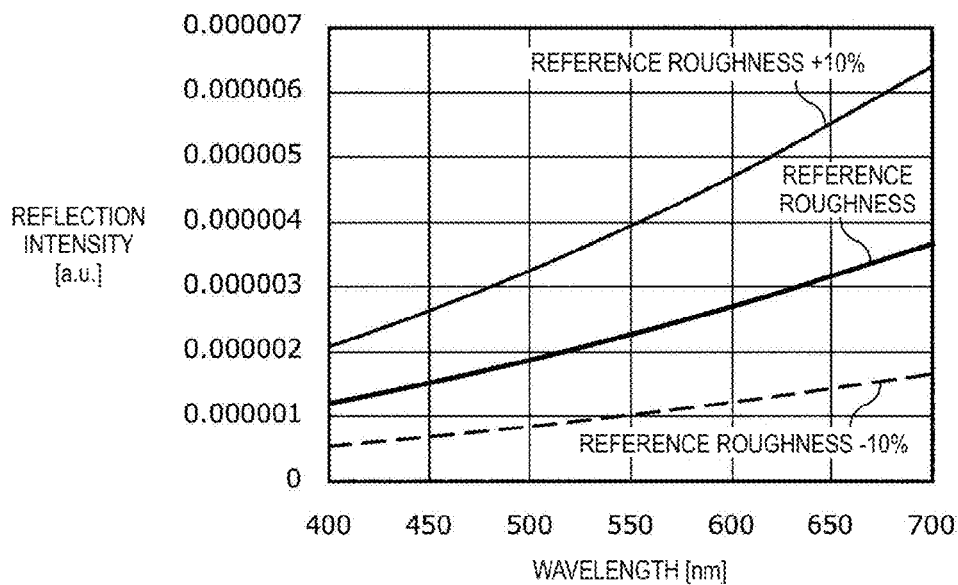
FIG. 11 is an explanatory diagram for explaining wavelengths of illumination light in a measurement apparatus according to the embodiment.

Focus on a case where an incident angle of illumination light is set to 45 degrees and the color line sensor camera 101 is installed perpendicularly in the normal direction to the surface (i.e., a case where $|\theta_1|$ and $|\theta_2|$ are each set to 45 degrees in FIG. 2A). In this case, reflection intensity based on the KBS model when surface roughness is set to 1.5 µm±10% and correlation length of surface roughness is set to 15 µm is calculated. FIG. 11 shows the obtained results. FIG. 11 reveals the following: (1) even at the same surface roughness, a change in the wavelength of incident light changes obtained reflection intensity; and (2) if surface roughness changes, reflection intensity changes even at the same wavelength of incident light.

Here, assume three types of wavelengths of a wavelength belonging to a blue band (460 nm), a wavelength belonging to a green band (530 nm), and a wavelength belonging to a red band (640 nm), as a peak wavelength of the first illumination light. On this occasion, a peak wavelength of the first illumination light is fixed at any one of the three types of wavelengths, and the relation between a peak wavelength of the second illumination light and an angle error is calculated and shown in FIGS. 12 to 14.

Figure 12:
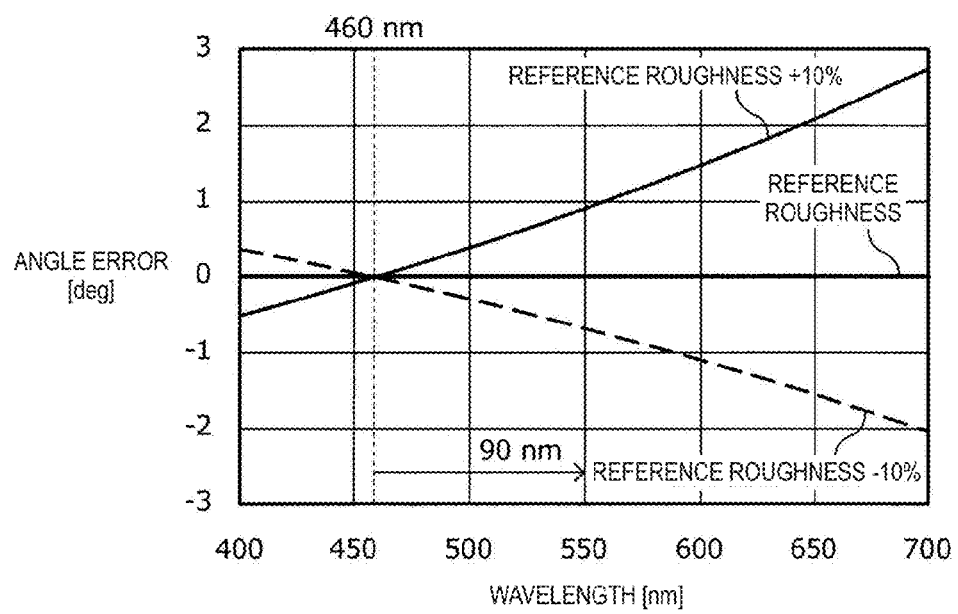
FIG. 12 is an explanatory diagram for explaining wavelengths of illumination light in a measurement apparatus according to the embodiment.

First, focus on FIG. 12. FIG. 12 shows a simulation of the relation between a peak wavelength of the second illumination light and an angle error when blue light with a peak wavelength of 460 nm is selected as the first illumination light, with regard to three types of surface roughness of reference roughness=1.5 µm, reference roughness+10%, and reference roughness−10%. As shown in FIG. 12, at the reference roughness=1.5 µm, the correction constant in the formula 101 is appropriately set for each peak wavelength of the second illumination light, so that the angle error is 0 degrees regardless of the peak wavelength of the second illumination light. However, when the surface roughness changes to the reference roughness+10% or the reference roughness −10%, the change cannot be corrected sufficiently even by using the correction constant decided regarding the reference roughness, which causes false inclination as shown in FIG. 7, resulting in an angle error.

The simulation results in FIG. 12 show that the angle error falls within ±1 degree when the peak wavelength of the second illumination light (the value of the horizontal axis) is within a range of the peak wavelength of the first illumination light (=460 nm)+90 nm.

Figure 13:
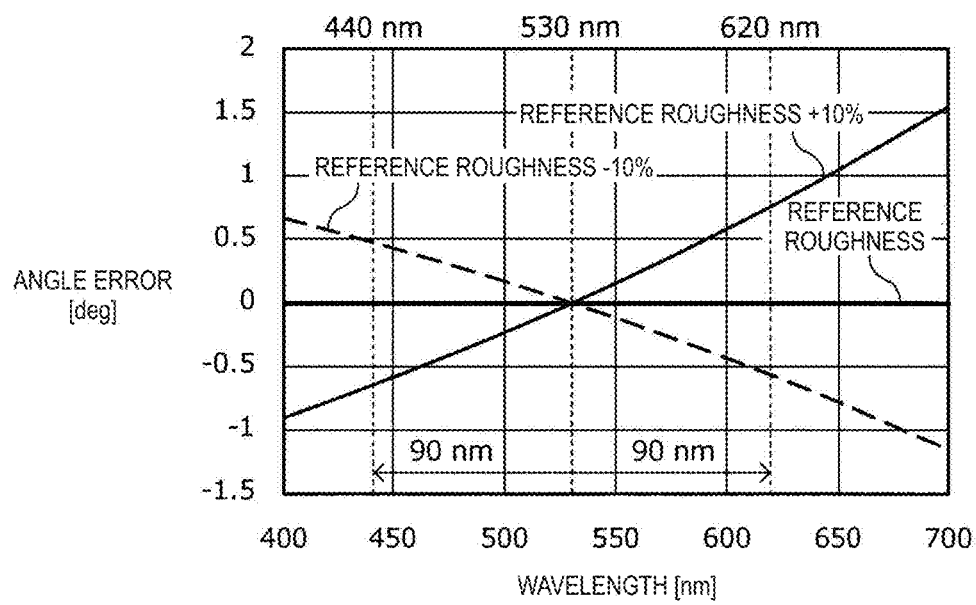
FIG. 13 is an explanatory diagram for explaining wavelengths of illumination light in a measurement apparatus according to the embodiment.

Next, focus on FIG. 13. FIG. 13 shows a simulation of the relation between a peak wavelength of the second illumination light and an angle error when green light with a peak wavelength of 530 nm is selected as the first illumination light, with regard to three types of surface roughness of reference roughness=1.5 µm, reference roughness+10%, and reference roughness−10%. Also in the case shown in FIG. 13, at the reference roughness=1.5 µm, the correction constant in the formula 101 is appropriately set for each peak wavelength of the second illumination light, so that the angle error is 0 degrees regardless of the peak wavelength of the second illumination light. However, when the surface roughness changes to the reference roughness+10% or the reference roughness−10%, the change cannot be corrected sufficiently even by using the correction constant decided regarding the reference roughness, which causes false inclination as shown in FIG. 7, resulting in an angle error.

Here, check the angle error in FIG. 13 in a region of a range of 90 nm from the peak wavelength of the first illumination light, which is obtained by focusing on FIG. 12; the angle error falls within 1 degree in a band range of 440 nm to 620 nm.

Figure 14:
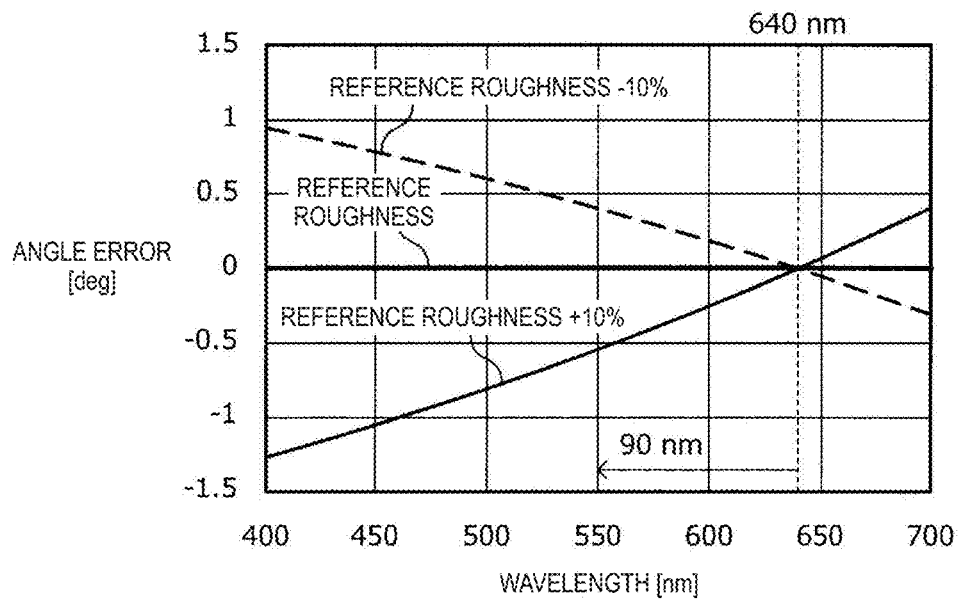
FIG. 14 is an explanatory diagram for explaining wavelengths of illumination light in a measurement apparatus according to the embodiment.

Similarly, focus on FIG. 14. FIG. 14 shows a simulation of the relation between a peak wavelength of the second illumination light and an angle error when red light with a peak wavelength of 640 nm is selected as the first illumination light, with regard to three types of surface roughness of reference roughness=1.5 µm, reference roughness+10%, and reference roughness−10%. Also in the case shown in FIG. 14, at the reference roughness=1.5 µm, the correction constant in the formula 101 is appropriately set for each peak wavelength of the second illumination light, so that the angle error is 0 degrees regardless of the peak wavelength of the second illumination light. However, when the surface roughness changes to the reference roughness+10% or the reference roughness−10%, the change cannot be corrected sufficiently even by using the correction constant decided regarding the reference roughness, which causes false inclination as shown in FIG. 7, resulting in an angle error.

Here, also in FIG. 14, check the angle error in a region of a range of 90 nm from the peak wavelength of the first illumination light; the angle error falls within 1 degree in a band range of 550 nm to 640 nm.

According to the findings based on FIGS. 12 to 14, when a difference between the peak wavelength of the first illumination light and the peak wavelength of the second illumination light is set to 90 nm or less, a calculation error of surface inclination can be 1 degree or less with respect to a roughness change of 10%.

Hence, in the measurement apparatus 100 according to the present embodiment, the upper limit value of a difference between the peak wavelength of the first illumination light and the peak wavelength of the second illumination light is set to 90 nm. In the case where the peak wavelength of the first illumination light and the peak wavelength of the second illumination light are selected, the two wavelengths may be selected in a manner that the peak wavelengths have a difference of 90 nm or less and are mutually different.

The upper limit value of a difference between peak wavelengths of two illumination light beams has been described in detail with reference to FIGS. 5 to 14.

A luminance difference between two illumination light beams is defined as in the formula 101 in the above description, but, needless to say, the luminance difference may be defined as in the following formula 103.

luminance difference=(luminance value for color 2)−(luminance value for color 1)−correction constant (formula 103)

Lower Limit Value of Difference Between Peak Wavelengths of Two Illumination Light Beams Next, the lower limit value of a difference between peak wavelengths of two illumination light beams will be described in detail with reference to FIGS. 15 to 19.

Figure 15:
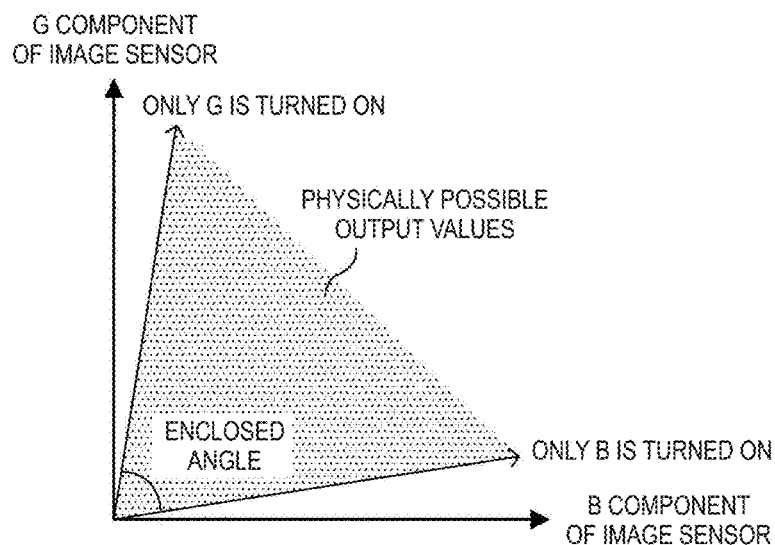
FIG. 15 is an explanatory diagram for explaining wavelengths of illumination light in a measurement apparatus according to the embodiment.

In shape inspection using two types of colored light, which is focused on in the shape inspection apparatus 10 according to the present embodiment, assume a case where sensitivity characteristics of the color line sensor camera 101 or emission spectra of two illumination light beams include an overlap. In such a case, as a result of color mixing, output values of two colors from the color line sensor camera 101 are present in a region enclosed by a straight line obtained when only the first illumination light is turned on and intensity is changed (e.g., a straight line obtained when only B is turned on in FIG. 15) and a straight line obtained when only the second illumination light is turned on and intensity is changed (e.g., a straight line obtained when only G is turned on in FIG. 15), as shown in FIG. 15 for example. In the following description, an angle that is formed by two straight lines each obtained when only one illumination light beam is turned on, as shown in FIG. 15, will be called an enclosed angle.

A large overlap of emission spectra of illumination light increases the degree of color mixing, consequently making the enclosed angle in FIG. 15 small. Conversely, a small overlap of emission spectra of illumination light does not increase the degree of color mixing so much, consequently making the enclosed angle in FIG. 15 approach 90 degrees.

Figure 16:
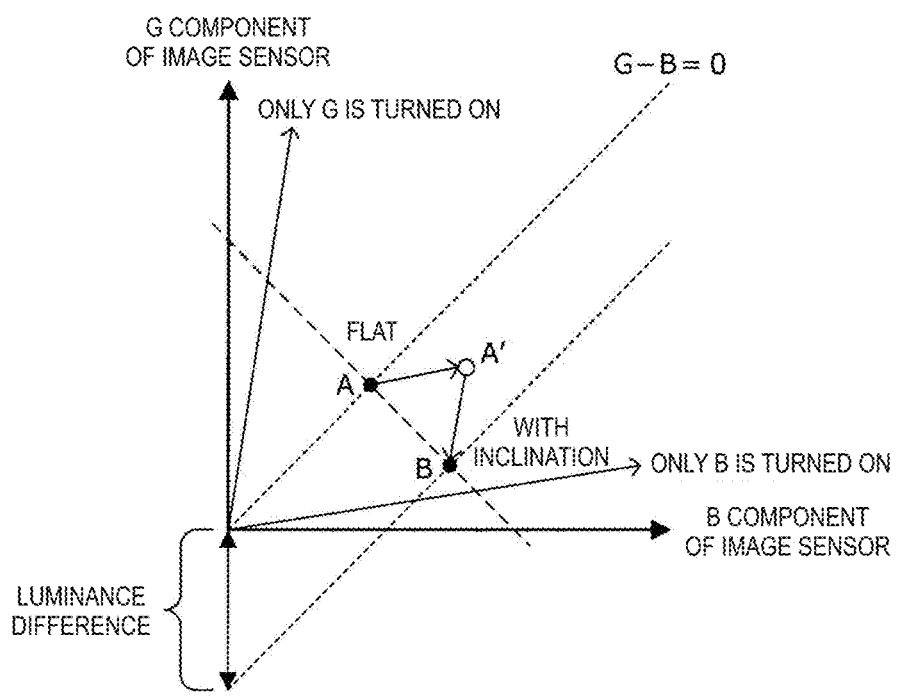
FIG. 16 is an explanatory diagram for explaining wavelengths of illumination light in a measurement apparatus according to the embodiment.

Assume that an intensity change due to an inclination of the surface of the metallic body S is linearly approximated and two illumination colors are equal in the amount of change. In the case where this assumption holds, an increase of an output value of color 1 is the same value as a decrease of an output value of color 2 in an image sensor provided in the color line sensor camera 101. Accordingly, as shown in FIG. 16, an output value from the image sensor regarding a flat surface changes along a straight line passing through the origin point of color 1−color 2=0 (in the example of FIG. 16, G−B=0) and having an inclination of 45 degrees. In FIG. 16, assume that in the case where an output value A is output regarding the flat surface, inclination of the surface causes the B component to increase from point A to point A' along a straight line having the same inclination as "a straight line obtained when only B is turned on". In this case, since a decrease of output of the G component is equal to an increase of output of the B component, the G component decreases from point A' to point B along a straight line having the same inclination as "a straight line obtained when only G is turned on". Consequently, the output value from the color line sensor camera 101 becomes the value at point B in FIG. 16. A luminance difference corresponding to the inclination in this case corresponds to a difference between the origin point and the y intercept of a straight line passing through point B and having an inclination of 45 degrees, as shown in FIG. 16.

Figure 17:
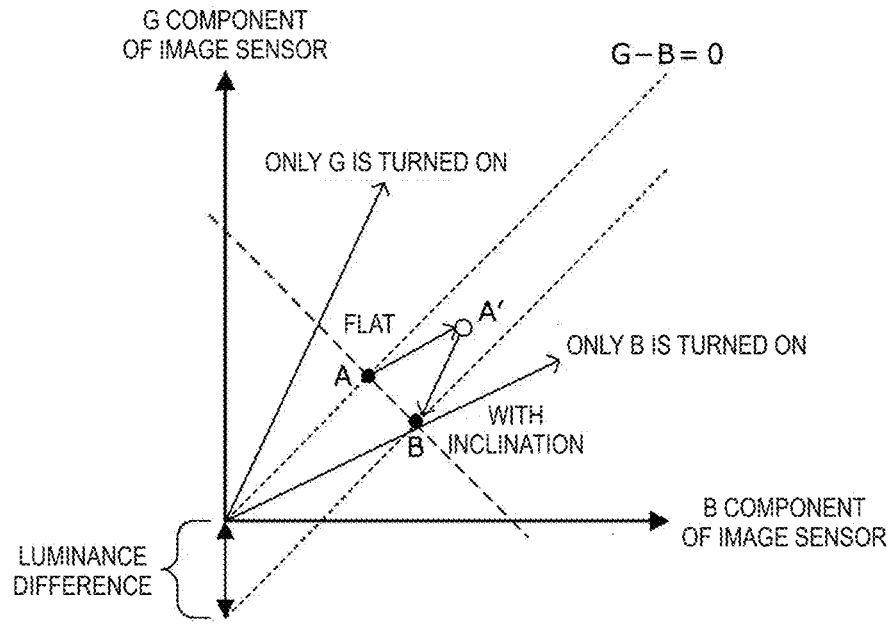
FIG. 17 is an explanatory diagram for explaining wavelengths of illumination light in a measurement apparatus according to the embodiment.

Moreover, a great degree of color mixing of two illumination light beams makes the enclosed angle smaller as shown in FIG. 17, consequently making a luminance difference smaller than that with a small degree of color mixing shown in FIG. 16.

On the other hand, camera noise overlaps the output from the image sensor provided in the color line sensor camera 101, the camera noise being independent for each of pixel components (R component, B component, and G component). Assuming that the camera noise adheres to Gauss distribution, the camera noise is expressed by a two-dimensional Gaussian function in a pixel component plane like a B-G plane shown in FIG. 18, exhibiting circular distribution as shown in FIG. 18 in the pixel component plane.

Figure 18:
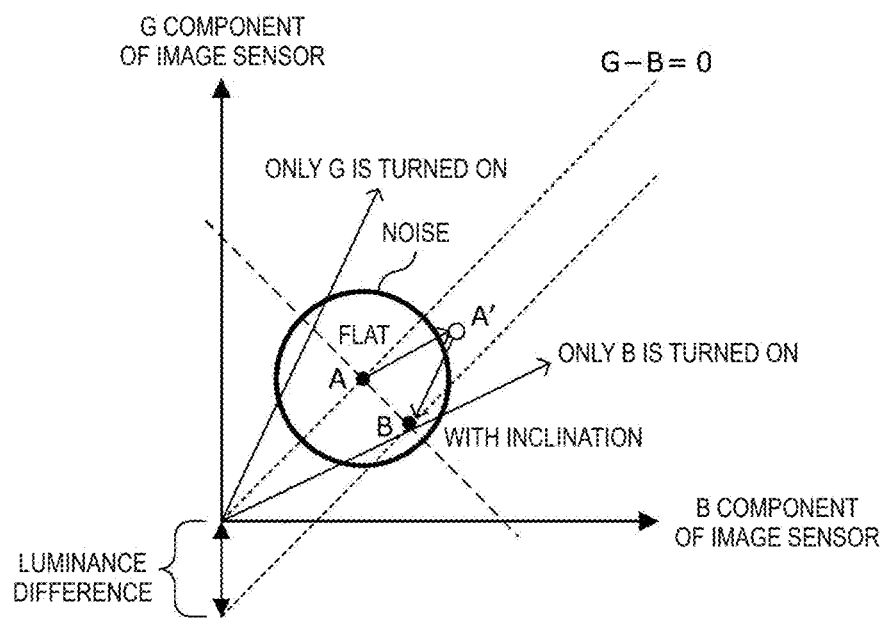
FIG. 18 is an explanatory diagram for explaining wavelengths of illumination light in a measurement apparatus according to the embodiment.

To prevent the output of the first illumination light and the second illumination light from being buried in camera noise, it is necessary to make the enclosed angle larger than a diameter of Gaussian noise shown in FIG. 18.

A color mixing matrix M expressing the degree of color mixing in the image sensor can be expressed by the following formula 105. Here, a matrix component $M_{ij}$ is expressed by the following formula, where a wavelength serves as a variable of integration.

$M_{ij}$=∫(emission spectrum of illumination $i$)×(spectral sensitivity of color $j$)$d\lambda$     [Math. 1]

When the degree of color mixing (i.e., matrix components $M_{12}$, $M_{21}$) when two illumination light beams are each turned on alone is normalized in a manner that intensity at the same color side is 1, a color mixing matrix $M_{norm}$ is expressed by the following formula 105'. Consequently, the pixel component plane shown in FIG. 18 is expressed as shown in FIG. 19. Here, two straight lines in FIG. 19 correspond to $M_{21}/M_{11}$ and $M_{12}/M_{22}$ in the formula 105'.

[Math. 2]

$$M = \begin{bmatrix} M_{11} & M_{12} \\ M_{21} & M_{22} \end{bmatrix} \quad \text{(formula 105)}$$

$$M_{norm} = \begin{bmatrix} 1 & M_{12}/M_{22} \\ M_{21}/M_{11} & 1 \end{bmatrix} \quad \text{(formula 105')}$$

Assume that a full width at half maximum (FWHM) of an emission spectrum of illumination light is 20 nm, which is a general full width at half maximum of an LED, a general illumination light source, a width of spectral sensitivity of the color line sensor camera is 50 nm in reference to a value of a general color filter that has the narrowest band, and a radius of Gaussian noise is 2% of the maximum output of the image sensor. In this case, the positional relation between the radius of the Gaussian noise and the enclosed angle formed by the two straight lines shown in FIG. 19 (the straight line corresponding to $M_{21}/M_{11}$ and the straight line corresponding to $M_{12}/M_{22}$) is simulated while a difference between peak wavelengths of two illumination light beams is changed. The simulation reveals that when the difference between peak wavelengths of two illumination light beams is less than 5 nm, a circle corresponding to the Gaussian noise extends beyond a region enclosed by the two straight lines.

According to these findings, the lower limit value of a difference between the peak wavelength of the first illumination light and the peak wavelength of the second illumination light is set to 5 nm in the measurement apparatus 100 according to the present embodiment.

The lower limit value of a difference between peak wavelengths of two illumination light beams has been described in detail with reference to FIGS. 15 to 19.

On the basis of the findings about the upper limit value and the lower limit value described above, in the measurement apparatus 100 according to the present embodiment, peak wavelengths of two illumination light beams are selected in a manner that the peak wavelength of the first illumination light and the peak wavelength of the second illumination light have a wavelength difference of equal to or more than 5 nm and equal to or less than 90 nm and are mutually different.

As the peak wavelengths of two illumination light beams actually selected, any wavelengths can be selected as long as the relation mentioned above is satisfied; for example, it is preferable that the peak wavelength of the first illumination light be selected from a wavelength band of 450 nm to 470 nm, and the peak wavelength of the second illumination light be selected from a wavelength band of 510 nm to 540 nm. When each peak wavelength is selected from the corresponding wavelength band, the first illumination light is blue light and the second illumination light is green light.

It is possible to prepare two types of band-pass filters described below, and further install each band-pass filter on the optical axis between the corresponding illumination light source and the metallic body S. That is, a first band-pass filter that transmits the first illumination light and a second band-pass filter that transmits the second illumination light are prepared, and a wavelength difference between a peak wavelength of a transmission band of the first band-pass filter and a peak wavelength of a transmission band of the second band-pass filter is set to a value of equal to or more than 5 nm and equal to or less than 90 nm. Then, the first band-pass filter is provided on the optical axis between the first illumination light source 103 and the metallic body S, and the second band-pass filter is provided on the optical axis between the second illumination light source 105 and the metallic body S. In this manner, the above-described wavelength difference between the peak wavelength of the first illumination light and the peak wavelength of the second illumination light can be achieved further reliably.

[Modification Example of Measurement Apparatus 100]

Here, there may be a case where the surface of the target metallic body S has high mirror polishability and surface roughness exhibits a small value, such as root-mean-square roughness Rq of 1 μm. In such a case, as shown in FIG. 5, a luminance value of reflected light that forms an image in the color line sensor camera 101 is a small value with regard to both of the two illumination light sources.

Now an illumination light source that emits illumination light with a peak wavelength of 530 nm and an illumination light source that emits illumination light with a peak wavelength of 460 nm are installed with $|\theta_1|$ and $|\theta_2|$ illustrated in FIG. 2A each set to 45 degrees to the color line sensor camera 101. On this occasion, root-mean-square roughness Rq is set to 1.0 μm, correlation length is set to 15 μm, and an incident angle is set to 45 degrees on the basis of the KBS model, intensity of reflected light that forms an image in the color line sensor camera 101 is calculated, and a luminance difference between two reflected light beams is calculated and shown in FIG. 20.

FIG. 20 reveals that in the graph showing the luminance difference, the amount of change in inclination is slight in the vicinity of an inclination angle φ of 0 degrees, which is shown as a region surrounded by a chain line, because the inclination is substantially zero. Such a state means that in the vicinity of an inclination angle φ of 0 degrees, a change in inclination angle hardly causes a change in luminance difference, which leads to a large error in converting a luminance difference into an inclination angle. Hence, to perform shape inspection of the metallic body S further accurately even when the metallic body S has high mirror polishability, a third illumination light source 151 that emits third illumination light having a peak wavelength that differs from those of the first illumination light and the second illumination light by 5 nm or more may be installed in the vicinity of a direction of regular reflection of the optical axis of the color line sensor camera 101 at the surface of the metallic body S, as illustrated in FIGS. 21 and 22.

Also for the third illumination light source 151, it is possible to prepare a third band-pass filter whose transmission band has a peak wavelength that differs from those of the transmission bands of the first band-pass filter and the second band-pass filter by 5 nm or more, and provide the third band-pass filter on the optical axis between the third illumination light source 151 and the metallic body S. In this manner, the relation that "the third illumination light has a peak wavelength that differs from those of the first illumination light and the second illumination light by 5 nm or more" can be achieved further reliably.

Here, the vicinity of the regular reflection direction of the color line sensor camera 101 includes not only a position along the regular reflection direction of the color line sensor camera 101 as illustrated in FIG. 22, but also a position separated from the regular reflection direction by a predetermined angle $\theta_3$ as illustrated in FIG. 21. Here, the angle $\theta_3$ of separation from the regular reflection direction is preferably set within a range allowing the color line sensor camera 101 to measure regular reflection of the third illumination light at the metallic body surface. This angle $\theta_3$ is further preferably 5 degrees or less, for example.

In the case where the peak wavelength of the first illumination light is set at a blue light band and the peak wavelength of the second illumination light is set at a green light band on the basis of the above-described criteria of peak wavelengths, the peak wavelength of the third illumination light may be set at a red light band (wavelength band of 600 to 700 nm).

Root-mean-square roughness Rq is set to 1.0 μm, correlation length is set to 15 μm, and an incident angle is set to 5 degrees (i.e., an angle at substantially regular reflection) on the basis of the KBS model, and intensity of reflected light that forms an image in the color line sensor camera 101 is calculated and shown in FIG. 23. FIG. 23 reveals that by providing the third illumination light source 151 in the vicinity of the regular reflection direction of the color line sensor camera 101, a straight line with a given inclination (e.g., a tangent line at the origin point of a luminance difference curve) can be set in the vicinity of an inclination angle of 0 degrees. Using this straight line makes it possible to further accurately calculate the inclination of the surface even when surface roughness Rq is as extremely small as 1 μm.

The modification example of the measurement apparatus 100 according to the present embodiment has been described with reference to FIGS. 20 to 23.

<Arithmetic Processing Apparatus 200>

Figure 24:
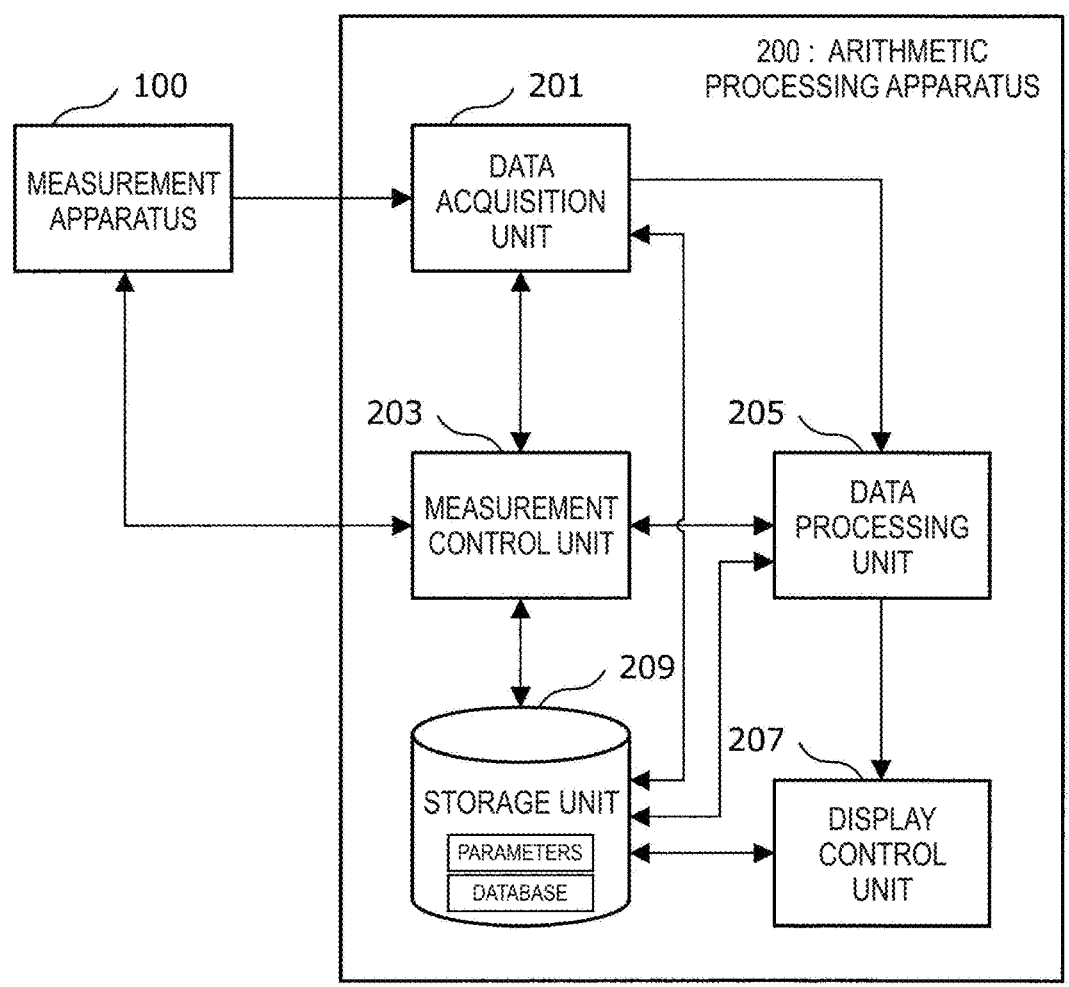
FIG. 24 is a block diagram illustrating an example of a configuration of an arithmetic processing apparatus included in a shape inspection apparatus according to the embodiment.

Now, a configuration of the arithmetic processing apparatus 200 included in the shape inspection apparatus 10 according to the present embodiment will be described in detail with reference to FIG. 24. The following description describes a case where the measurement apparatus 100 includes the first illumination light source 103, the second illumination light source 105, and the third illumination light source 151. Needless to say, a process related to the third illumination light source 151 in the following description is not performed in the case where the measurement apparatus 100 does not include the third illumination light source 151. FIG. 24 is a block diagram illustrating an example of an overall configuration of the arithmetic processing apparatus 200 according to the present embodiment.

The arithmetic processing apparatus 200 according to the present embodiment is an apparatus that calculates information for inspection used for shape inspection of the metallic body S, on the basis of luminance values of reflected light obtained by the measurement apparatus 100. In the arithmetic processing apparatus 200, at least information on an inclination of the surface of the metallic body S is calculated, and further, information on the surface shape of the metallic body S may be calculated, as the information for inspection.

As illustrated in FIG. 24, this arithmetic processing apparatus 200 mainly includes a data acquisition unit 201, a measurement control unit 203, a data processing unit 205, a display control unit 207, and a storage unit 209.

The data acquisition unit 201 is configured with, for example, a central processing unit (CPU), a read only memory (ROM), a random access memory (RAM), a communication device, and the like. The data acquisition unit 201 acquires data on luminance values of reflected light, which is generated and output by the measurement apparatus 100, and transmits the data to the data processing unit 205 described later. Moreover, the data acquisition unit 201 may contain the acquired data on the luminance values of the reflected light as history information in the storage unit 209 described later, in association with time information on date and time at which the data is acquired.

The measurement control unit 203 is configured with a CPU, a ROM, a RAM, a communication device, and the like. The measurement control unit 203 controls measurement of the metallic body S by the measurement apparatus 100 according to the present embodiment. Specifically, in starting the measurement of the metallic body S, the measurement control unit 203 sends controls signals for starting emission of illumination light beams to the first illumination light source 103, the second illumination light source 105, and the third illumination light source 151.

When the first illumination light source 103, the second illumination light source 105, and the third illumination light source 151 start to irradiate the surface of the metallic body S with the illumination light beams, the measurement control unit 203 sends a trigger signal for starting measurement to the color line sensor camera 101, on the basis of a PLG signal that is sent at regular intervals from a driving mechanism etc. for changing a relative position between the metallic body S and the measurement apparatus 100 (e.g., a PLG signal output each time the metallic body S moves 1 mm).

In this manner, the measurement apparatus 100 can generate measurement data (data on luminance values of reflected light) at each position of the metallic body S in the conveyance direction.

The data processing unit 205 is configured with, for example, a CPU, a ROM, a RAM, a communication device, and the like. The data processing unit 205 uses data on luminance values of reflected light, generated by the measurement apparatus 100, to perform data processing, which will be described later, on the data on the luminance values of the reflected light beams, and calculates information for inspection used for shape inspection of the metallic body S. Upon ending the calculation process of information for inspection, the data processing unit 205 transmits information on the obtained processing results to the display control unit 207.

This data processing unit 205 will be described in detail later.

The display control unit 207 is configured with, for example, a CPU, a ROM, a RAM, an output device, and the like. The display control unit 207 performs display control in displaying various processing results including calculation results of information for inspection on the metallic body S, which are transmitted from the data processing unit 205, on an output device (e.g., a display) included in the arithmetic processing apparatus 200, an output device provided outside the arithmetic processing apparatus 200, or the like. Thus, a user of the shape inspection apparatus 10 can recognize on-site various processing results, such as information for inspection on the metallic body S.

The storage unit 209 is configured with, for example, a RAM, a storage device, and the like included in the arithmetic processing apparatus 200 according to the present embodiment. In the storage unit 209, various parameters and process intermediate progresses that the arithmetic processing apparatus 200 according to the present embodiment needs to save when performing some sort of process, various databases and programs, or the like are recorded as appropriate. With regard to this storage unit 209, the data acquisition unit 201, the measurement control unit 203, the data processing unit 205, the display control unit 207, and the like can perform a data read/write process freely.

[Data Processing Unit 205]

Figure 25:
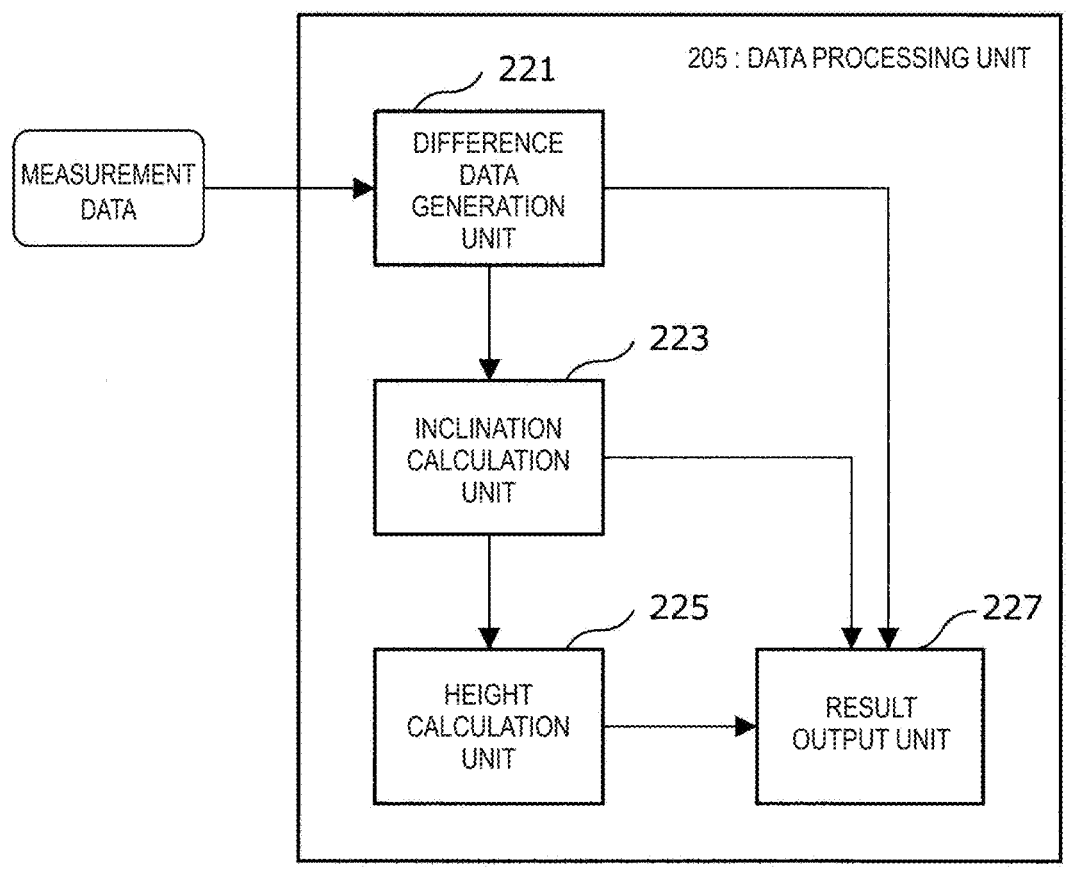
FIG. 25 is a block diagram illustrating an example of a configuration of a data processing unit included in an arithmetic processing apparatus according to the embodiment.
Figure 26:
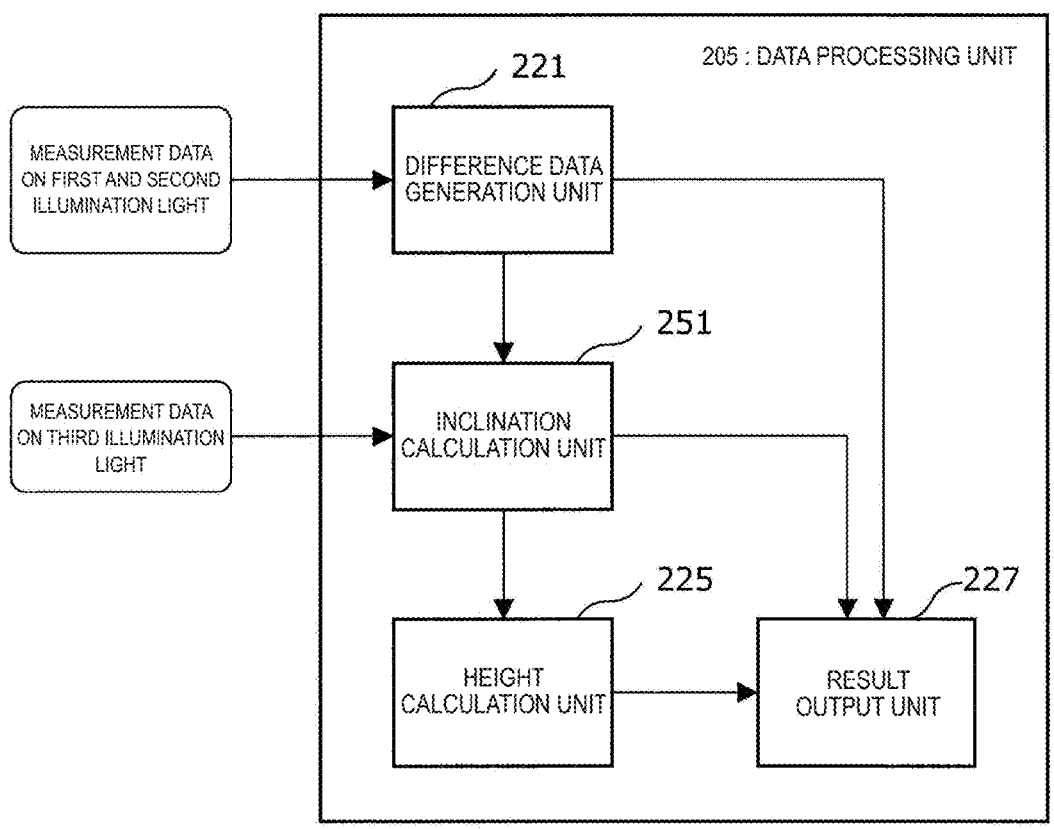
FIG. 26 is a block diagram illustrating another example of a configuration of a data processing unit included in an arithmetic processing apparatus according to the embodiment.

Next, a configuration of the data processing unit 205 included in the arithmetic processing apparatus 200 according to the present embodiment will be described in detail with reference to FIGS. 25 and 26. FIGS. 25 and 26 are block diagrams each illustrating an example of a configuration of the data processing unit 205 according to the present embodiment.

First, description will be given on details of data processing using luminance value data output from the measurement apparatus 100 provided with the first illumination light source 103 and the second illumination light source 105, with reference to FIG. 25.

The data processing unit 205 according to the present embodiment calculates information for inspection including at least information on an inclination of the surface of the metallic body S, on the basis of a difference (i.e., a luminance difference) between a luminance value of reflected light of the first illumination light and a luminance value of reflected light of the second illumination light. As illustrated in FIG. 25, this data processing unit 205 includes a difference data generation unit 221, an inclination calculation unit 223, a height calculation unit 225, and a result output unit 227.

The difference data generation unit 221 is configured with, for example, a CPU, a ROM, a RAM, and the like. The difference data generation unit 221 performs a difference data generation process (i.e., a luminance difference data generation process), which will be described later, on data on the luminance value of the reflected light of the first illumination light (hereinafter simply called "measurement data on the first illumination light") and data on the luminance value of the reflected light of the second illumination light (hereinafter simply called "measurement data on the second illumination light"), acquired by the data acquisition unit 201.

Hereinafter, the difference data generation process performed by the difference data generation unit 221 will be described.

The difference data generation unit 221 generates difference data (i.e., luminance difference data) composed of a difference between the measurement data on the first illumination light and the measurement data on the second illumination light, on the basis of the following formula 111 or formula 113, by using the measurement data on the first illumination light and the measurement data on the second illumination light.

difference between luminance values=(luminance value of reflected light of first illumination light)−(luminance value of reflected light of second illumination light)+correction constant   (formula 111)

difference between luminance values=(luminance value of reflected light of second illumination light)−(luminance value of reflected light of first illumination light)−correction constant   (formula 113)

Here, as have been described above, the correction constant in the formula 111 and the formula 113 is set in advance in a manner that the value of the right side of the formula 111 or the formula 113 is zero, by actually measuring the measurement data on the first illumination light and the measurement data on the second illumination light using a plane without inclination (i.e., a plane known to be flat).

Information on a value of the correction constant set in advance is contained in the storage unit 209, for example. In performing the difference data generation process, the difference data generation unit 221 acquires the information on the correction constant from the storage unit 209, and performs the difference data generation process.

The difference data generation unit 221 may use either one of the formula 111 and the formula 113, as long as the used formula is not changed during a shape inspection process for the metallic body S.

By performing the difference arithmetic process described above, the difference data generation unit 221 can obtain a data group of difference values (in other words, map data on difference values) for the entire surface of the metallic body S. The data group of difference values obtained in this manner serves as information for inspection used in inspecting the shape (specifically, surface shape) of the metallic body S. Moreover, the information for inspection can be imaged by replacing difference values included in the information for inspection with high/low of luminance values or light/dark. By imaging the generated map data on luminance differences into a difference image, shape inspection based on the difference image can be performed.

The difference data generation process as described above performed by the difference data generation unit 221 removes the influence of illumination irregularity, a formation pattern, a difference in reflectance, soil, etc. from measurement data, making it possible to precisely detect a microscopic shape.

The difference data generation unit 221 outputs the difference data (luminance difference data) generated in the above-described manner to the inclination calculation unit 223. In addition, the difference data generation unit 221 may output the generated difference data itself to the result output unit 227.

The inclination calculation unit 223 is configured with, for example, a CPU, a ROM, a RAM, and the like. The inclination calculation unit 223 calculates the direction and magnitude of an inclination of the surface of the metallic body S, on the basis of the relation between a luminance difference and an inclination, by using the difference data (luminance difference data) output from the difference data generation unit 221. As have been described above with reference to FIG. 10, a conversion coefficient for converting a luminance difference into an angle can be specified in advance, according to an inclination of the luminance difference graph in the vicinity of an inclination angle $\phi$ of 0 degrees.

FIG. 10 reveals that when the inclination of the graph near the origin point (i.e., the conversion coefficient) is denoted by $\alpha$, a luminance difference $\Delta L$ and the inclination angle $\phi$ can be expressed by a relation of $\Delta L = \alpha \times \phi$. Hence, the inclination calculation unit 223 can convert luminance differences $\Delta L$ into inclination angles $\phi$ of the surface by using a data group on $\Delta L$ output from the difference data generation unit 221, and the conversion coefficient $\alpha$. The inclination of the surface of the metallic body S of interest corresponds to a tangent at the inclination angle $\phi$ obtained by converting the luminance difference. Hence, the inclination calculation unit 223 calculates tan $\phi$, which is the tangent at the calculated inclination angle $\phi$, thereby calculating the inclination of the surface of the metallic body S of interest. The inclination calculated in this manner expresses the direction of the inclination by its sign, and expresses the specific magnitude of the inclination by its absolute value.

Information on the conversion coefficient specified in advance is contained in the storage unit 209, for example. In performing the inclination calculation process, the inclination calculation unit 223 acquires the information on the conversion coefficient from the storage unit 209, and converts the luminance difference into the inclination angle.

By performing the above-described process for all elements of the luminance difference data, the inclination calculation unit 223 can obtain a data group of inclination values (in other words, map data on inclination values) for the entire surface of the metallic body S. The data group of inclination values obtained in this manner serves as information for inspection used in inspecting the shape (specifically, surface shape) of the metallic body S. Moreover, the information for inspection can be imaged by replacing inclination values included in the information for inspection with high/low of luminance values or light/dark. By imaging the generated map data on inclinations into an inclination image, shape inspection based on the inclination image can be performed.

Moreover, the inclination calculation unit 223 can perform inspection of the surface shape of the metallic body S by comparing the calculated inclination with a predetermined threshold value. That is, a threshold value of the inclination of the surface when an abnormal portion is present at the surface of the metallic body S is specified in advance by performing known statistical processing or the like on the basis of operation data in the past, etc., and contained in the storage unit 209 or the like. Then, the inclination calculation unit 223 specifies the magnitude relation between the calculated inclination value and the threshold value, which makes it possible to inspect whether an abnormal portion is present at the surface of the metallic body S of interest.

The inclination calculation unit 223 outputs the data on an inclination of the surface of the metallic body S generated in the above-described manner to the height calculation unit 225. In addition, the inclination calculation unit 223 may output the generated data on an inclination of the surface of the metallic body S itself, or inspection results of the surface of the metallic body S to the result output unit 227.

The height calculation unit 225 is configured with, for example, a CPU, a ROM, a RAM, and the like. The height calculation unit 225 calculates the height of the surface of the metallic body S of interest by using the inclination of the surface of the metallic body S calculated by the inclination calculation unit 223. Specifically, the height calculation unit 225 integrates the inclination tamp of the surface of the metallic body S calculated by the inclination calculation unit 223 along the longitudinal direction of the metallic body S, which is the relative movement direction of the color line sensor camera 101 and the metallic body S (in other words, the scanning direction of the color line sensor camera 101), thereby calculating the height of the surface of the metallic body S.

By performing the above-described integrating process for all elements of the data on the inclinations of the surface, the height calculation unit 225 can obtain a data group on surface heights (in other words, map data on surface heights) for the entire surface of the metallic body S. The data group on surface heights obtained in this manner serves as information for inspection used in inspecting the shape (specifically, surface shape) of the metallic body S. Moreover, the information for inspection can be imaged by replacing surface height values included in the information for inspection with high/low of luminance values or light/dark. By imaging the generated map data on surface heights into a height image, shape inspection based on the height image can be performed.

The height calculation unit 225 outputs the data on the height of the surface of the metallic body S generated in the above-described manner to the result output unit 227.

The result output unit 227 is configured with, for example, a CPU, a ROM, a RAM, and the like. The result output unit 227 outputs various types of information on shape inspection results of the metallic body, such as luminance difference data generated by the difference data generation unit 221, data on the inclination of the surface of the metallic body S or inspection results calculated by the inclination calculation unit 223, and data on the height of the surface of the metallic body S calculated by the height calculation unit 225, to the display control unit 207. Thus, various types of information on shape inspection results of the metallic body S is output to a display unit (not illustrated). The result output unit 227 may also output the obtained shape inspection results to an external device such as a process computer system for production management, and may create various record files relevant to products by utilizing the obtained shape inspection results. Moreover, the result output unit 227 may contain information on the shape inspection results of the metallic body S, as history information, in the storage unit 209 or the like, in association with time information on date and time at which the information is calculated.

The configuration of the data processing unit 205 when shape inspection of the metallic body S is performed using the measurement data on the first illumination light and the measurement data on the second illumination light has been described in detail with reference to FIG. 25.

In the case where the measurement apparatus 100 is provided with the third illumination light source 151 as illustrated in FIGS. 21 and 22, data on a luminance value of reflected light of the third illumination light (hereinafter simply called "measurement data on the third illumination light") can be used in addition to the measurement data on the first illumination light and the second illumination light. Hence, the following description briefly describes a configuration of the data processing unit 205 when shape inspection of the metallic body S is performed using measurement data on the first to third illumination light, with reference to FIG. 26.

The data processing unit 205 that performs such processing includes the difference data generation unit 221, an inclination calculation unit 251, the height calculation unit 225, and the result output unit 227, as illustrated in FIG. 26.

Here, the measurement data on the first illumination light and the second illumination light acquired by the data acquisition unit 201 is output to the difference data generation unit 221, and the measurement data on the third illumination light acquired by the data acquisition unit 201 is output to the inclination calculation unit 251, as illustrated in FIG. 26.

A difference data generation process performed in the difference data generation unit 221 illustrated in FIG. 26 is similar to the difference data generation process illustrated in FIG. 25, and thus detailed description thereof is omitted.

The inclination calculation unit 251 is configured with, for example, a CPU, a ROM, a RAM, and the like. The inclination calculation unit 251 calculates the direction and magnitude of an inclination of the surface of the metallic body S, on the basis of the relation between a luminance difference and an inclination and the relation between a luminance value and an inclination, by using the difference data (luminance difference data) output from the difference data generation unit 221 and the measurement data on the third illumination light itself output from the data acquisition unit 201.

Specifically, the inclination calculation unit 251 calculates an inclination angle φ of the surface of the metallic body S of interest by using the luminance difference data in a manner similar to that of the inclination calculation process in the inclination calculation unit 223 illustrated in FIG. 25. Moreover, when luminance difference data to be processed is equal to or less than a predetermined threshold value, the inclination calculation unit 251 uses the measurement data on the third illumination light, instead of the luminance difference data, to calculate an inclination angle φ of the surface at a corresponding data position.

Here, as shown in FIG. 23 for example, also for measurement data on luminance values obtained using the third illumination light source 151 provided in the vicinity of a regular reflection position of the color line sensor camera 101, a conversion coefficient for converting a luminance value into an inclination can be decided by focusing on, for example, a tangent line of a luminance value curve in the vicinity of an inclination angle φ of 0 degrees. Hence, a conversion coefficient for converting a luminance value into an inclination is specified in advance and information on the conversion coefficient is contained in the storage unit 209, for example. In performing the inclination calculation process using the measurement data on the third illumination light, the inclination calculation unit 251 acquires the information on the conversion coefficient from the storage unit 209, and converts a luminance value into an inclination angle.

Then, the inclination calculation unit 251 adopts inclination data calculated from an inclination angle obtained by converting the luminance value, instead of inclination data obtained by converting a luminance difference, as inclination data at the data position of interest. In this manner, even for a data position that may greatly include errors when a luminance difference is used, the inclination of the surface can be obtained accurately by using the measurement data on the third illumination light.

Moreover, like the inclination calculation unit 223 illustrated in FIG. 25, the inclination calculation unit 251 can perform inspection of the surface shape of the metallic body S by comparing the calculated inclination with a predetermined threshold value.

The inclination calculation unit 251 outputs the data on an inclination of the surface of the metallic body S generated in the above-described manner to the height calculation unit 225. In addition, the inclination calculation unit 251 may output the generated data on an inclination of the surface of the metallic body S itself, or inspection results of the surface of the metallic body S to the result output unit 227.

Processes performed in the height calculation unit 225 and the result output unit 227 illustrated in FIG. 26 are similar to the processes performed in the height calculation unit 225 and the result output unit 227 illustrated in FIG. 25, and thus detailed description thereof is omitted.

An example of the function of the arithmetic processing apparatus 200 according to the present embodiment has been illustrated. Each of the above structural elements may be configured with a general-purpose member or circuit, and may be configured with hardware specialized for the function of each structural element. A CPU or the like may perform all of the functions of respective structural elements. Thus, a utilized configuration can be changed as appropriate, according to the technology level at the time of performing the present embodiment.

Note that the computer program for providing each function of the arithmetic processing apparatus according to the above present embodiment can be created and implemented in a personal computer or the like. Moreover, a computer-readable recording medium that contains this computer program can be provided as well. For example, the recording medium is a magnetic disk, an optical disc, a magneto-optical disk, a flash memory, or the like. The above computer program may be delivered via a network for example, without using the recording medium.

(Sequence of Shape Inspection Method)

Figure 27:
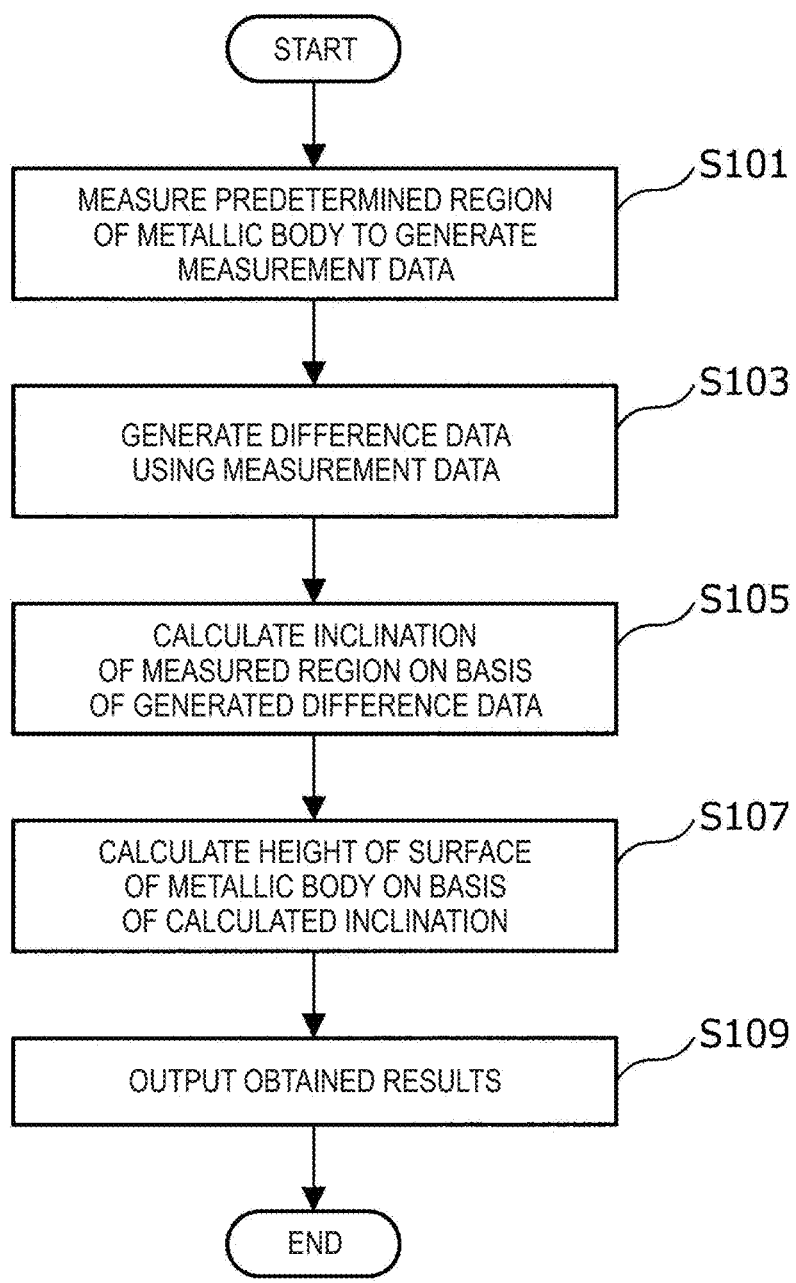
FIG. 27 is a flowchart showing an example of a sequence of a shape inspection method according to the embodiment.
Figure 28:
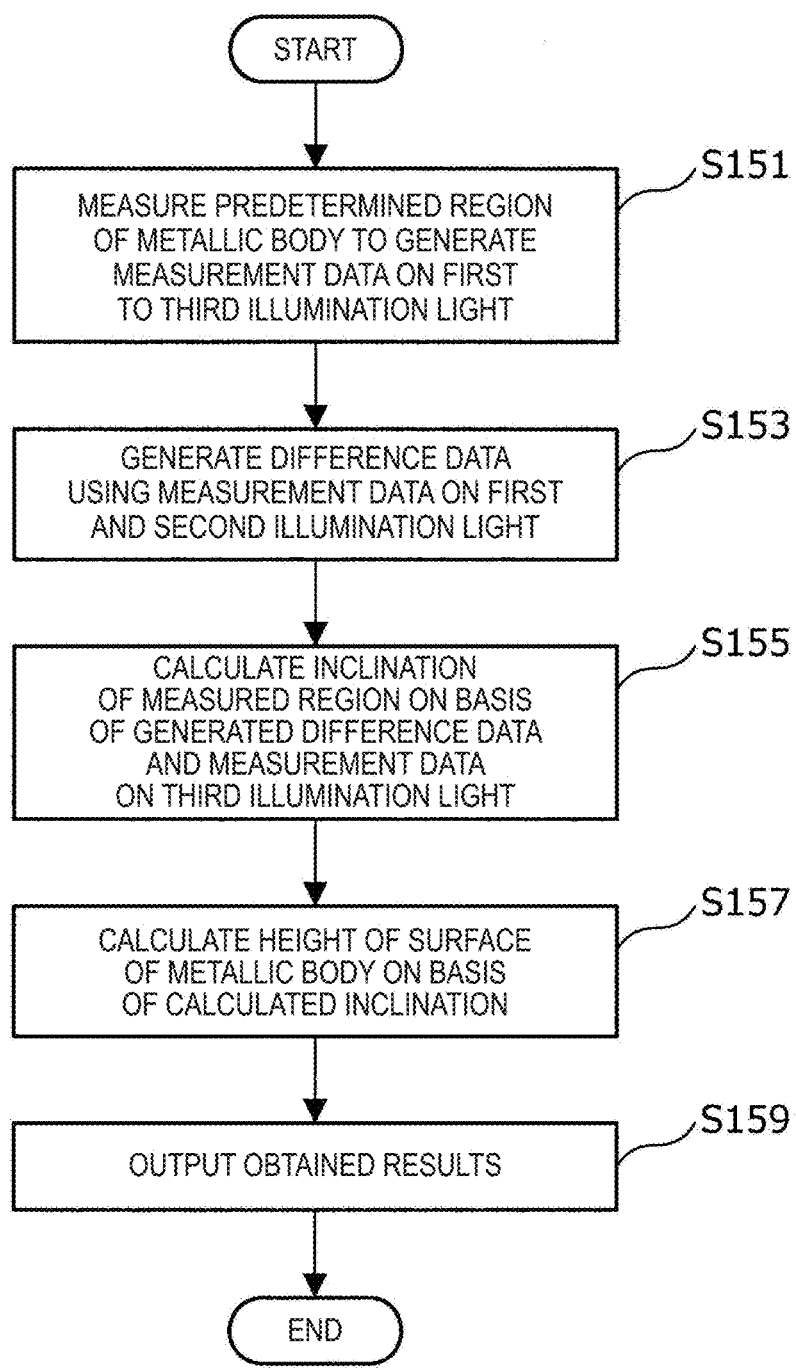
FIG. 28 is a flowchart showing another example of a sequence of a shape inspection method according to the embodiment.

Now, an example of a sequence of a shape inspection method performed in the shape inspection apparatus 10 according to the present embodiment will be described briefly with reference to FIGS. 27 and 28. FIGS. 27 and 28 are flowcharts each showing an example of a sequence of a shape inspection method according to the present embodiment.

First, an example of a sequence of a shape inspection method performed in the shape inspection apparatus 10 including the data processing unit 205 illustrated in FIG. 25 will be described briefly with reference to FIG. 27.

The measurement apparatus 100 of the shape inspection apparatus 10, under control of the measurement control unit 203 of the arithmetic processing apparatus 200, measures a predetermined region of the surface of the metallic body S by using the first illumination light and the second illumination light to generate measurement data on respective illumination light beams (step S101). After that, the measurement apparatus 100 outputs the generated measurement data to the arithmetic processing apparatus 200.

Upon acquiring the measurement data output from the measurement apparatus 100, the data acquisition unit 201 of the arithmetic processing apparatus 200 outputs the acquired measurement data to the difference data generation unit 221 of the data processing unit 205.

The difference data generation unit 221 of the data processing unit 205 generates difference data (i.e., luminance difference data) by the above-described process by using the measurement data on the first illumination light and the measurement data on the second illumination light (step S103). After that, the difference data generation unit 221 outputs the generated luminance difference data to the inclination calculation unit 223.

The inclination calculation unit 223 calculates data on an inclination of the surface of the metallic body S of interest (i.e., an inclination of the measured region) by using difference data (luminance difference data) output from the difference data generation unit 221 (step S105). After that, the inclination calculation unit 223 outputs the calculated data on inclination to the height calculation unit 225.

After that, the height calculation unit 225 integrates inclinations contained in the data on inclination output from the inclination calculation unit 223, thereby calculating the height of the surface of the metallic body (step S107). The height calculation unit 225 outputs the obtained data on the height of the surface of the metallic body to the result output unit 227.

When various types of information for inspection used for surface inspection of the metallic body S is input, the result output unit 227 outputs the obtained results to a user or various devices provided outside (step S109). Thus, the user can recognize inspection results on the shape of the metallic body S.

Next, an example of a sequence of a shape inspection method performed in the shape inspection apparatus 10 including the data processing unit 205 illustrated in FIG. 26 will be described briefly with reference to FIG. 28.

First, the measurement apparatus 100 of the shape inspection apparatus 10, under control of the measurement control unit 203 of the arithmetic processing apparatus 200, measures a predetermined region of the surface of the metallic body S by using the first illumination light to the third illumination light to generate measurement data on respective illumination light beams (step S151). After that, the measurement apparatus 100 outputs the generated measurement data to the arithmetic processing apparatus 200.

Upon acquiring the measurement data output from the measurement apparatus 100, the data acquisition unit 201 of the arithmetic processing apparatus 200 outputs the measurement data on the first illumination light and the second illumination light among the acquired measurement data to the difference data generation unit 221 of the data processing unit 205. In addition, the data acquisition unit 201 outputs the measurement data on the third illumination light among the acquired measurement data to the inclination calculation unit 251.

The difference data generation unit 221 of the data processing unit 205 generates difference data (i.e., luminance difference data) by the above-described process by using the measurement data on the first illumination light and the measurement data on the second illumination light (step S153). After that, the difference data generation unit 221 outputs the generated luminance difference data to the inclination calculation unit 251.

The inclination calculation unit 251 calculates data on an inclination of the surface of the metallic body S of interest (i.e., an inclination of the measured region) by the above-described process by using difference data (luminance difference data) output from the difference data generation unit 221 and the measurement data on the third illumination light (step S155). After that, the inclination calculation unit 251 outputs the calculated data on inclination to the height calculation unit 225.

After that, the height calculation unit 225 integrates inclinations contained in the data on inclination output from the inclination calculation unit 223, thereby calculating the height of the surface of the metallic body (step S157). The height calculation unit 225 outputs the obtained data on the height of the surface of the metallic body to the result output unit 227.

When various types of information for inspection used for surface inspection of the metallic body S is input, the result output unit 227 outputs the obtained results to a user or various devices provided outside (step S159). Thus, the user can recognize inspection results on the shape of the metallic body S.

An example of a shape inspection method performed in the shape inspection apparatus 10 according to the present embodiment has been described briefly with reference to FIGS. 27 and 28.

(Hardware Configuration)

Figure 29:
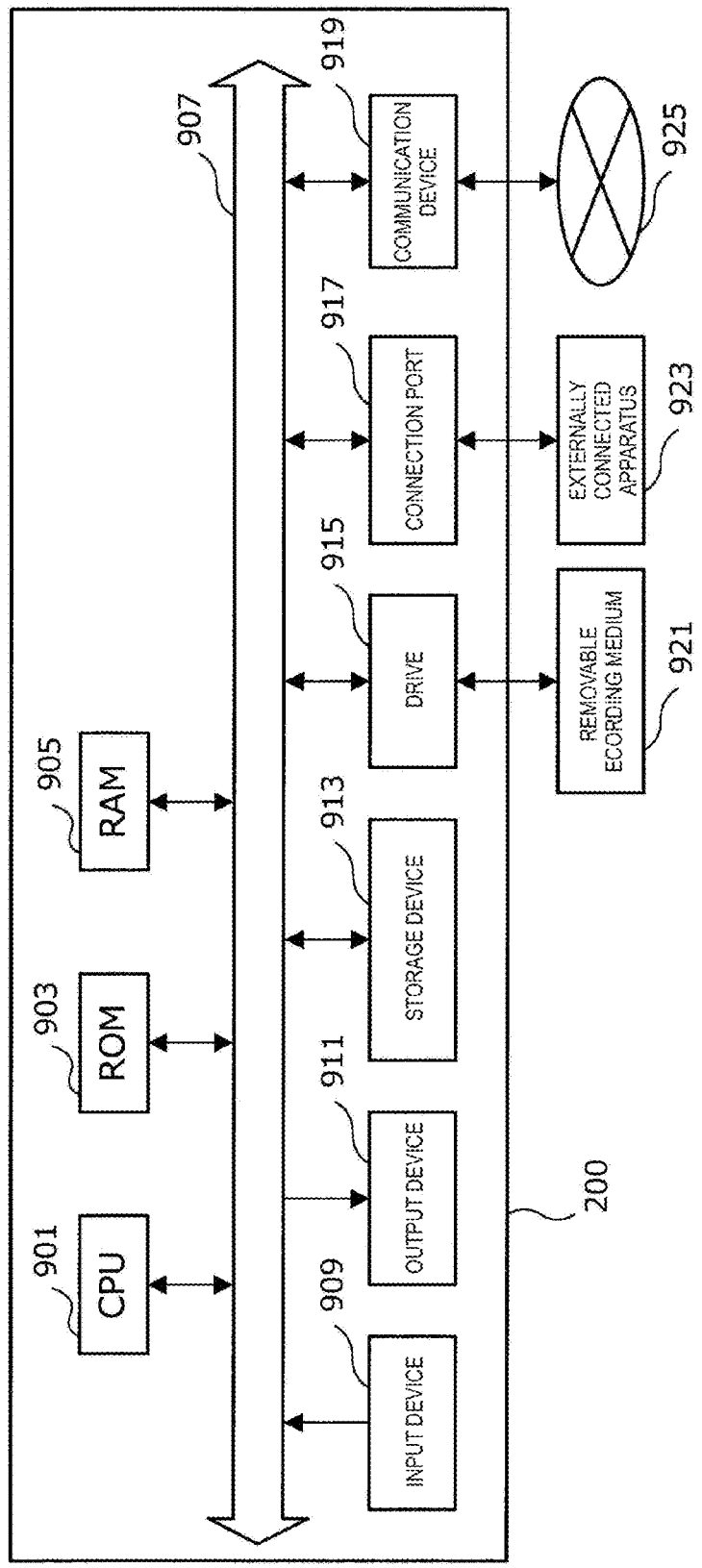
FIG. 29 is a block diagram illustrating an example of a hardware configuration of an arithmetic processing apparatus according to an embodiment of the present invention.

Next, the hardware configuration of the arithmetic processing apparatus 200 according to an embodiment of the present invention will be described in detail with reference to FIG. 29. FIG. 29 is a block diagram for explaining the hardware configuration of the arithmetic processing apparatus 200 according to an embodiment of the present invention.

The arithmetic processing apparatus 200 mainly includes a CPU 901, a ROM 903, and a RAM 905. Furthermore, the arithmetic processing apparatus 200 also includes a bus 907, an input device 909, an output device 911, a storage device 913, a drive 915, a connection port 917, and a communication device 919.

The CPU 901 serves as a central processing apparatus and a control device, and controls the overall operation or a part of the operation of the arithmetic processing apparatus 200 according to various programs recorded in the ROM 903, the RAM 905, the storage device 913, or a removable recording medium 921. The ROM 903 stores programs, operation parameters, and the like used by the CPU 901. The RAM 905 primarily stores programs that the CPU 901 uses and parameters and the like varying as appropriate during the execution of the programs. These are connected with each other via the bus 907 configured from an internal bus such as a CPU bus or the like.

The bus 907 is connected to the external bus such as a PCI (Peripheral Component Interconnect/Interface) bus via the bridge.

The input device 909 is an operation means operated by a user, such as a mouse, a keyboard, a touch panel, buttons, a switch and a lever. The input device 909 may be a remote control means (a so-called remote control) using, for example, infrared light or other radio waves, or may be an externally connected apparatus 923 such as a PDA conforming to the operation of the arithmetic processing apparatus 200. Furthermore, the input device 909 generates an input signal based on, for example, information which is input by a user with the above operation means, and is configured from an input control circuit for outputting the input signal to the CPU 901. The user can input various data to the shape inspection apparatus 10 and can instruct the shape inspection apparatus 10 to perform processing by operating this input device 909.

The output device 911 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 911 outputs a result obtained by various processes performed by the arithmetic processing apparatus 200. More specifically, the display device displays, in the form of texts or images, a result obtained by various processes performed by the arithmetic processing apparatus 200. On the other hand, the audio output device converts an audio signal such as reproduced audio data and sound data into an analog signal, and outputs the analog signal.

The storage device 913 is a device for storing data configured as an example of a storage unit of the arithmetic processing apparatus 200 and is used to store data. The storage device 913 is configured from, for example, a magnetic storage device such as a HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for recording medium, and is embedded in the arithmetic processing apparatus 200 or attached externally thereto. The drive 915 reads information recorded in the attached removable recording medium 921 such as a magnetic disk, an optical disk, a magneto-optical disk, or a semiconductor memory, and outputs the read information to the RAM 905. Furthermore, the drive 915 can write in the attached removable recording medium 921 such as a magnetic disk, an optical disk, a magneto-optical disk, or a semiconductor memory. The removable recording medium 921 is, for example, a CD medium, a DVD medium, or a Blu-ray medium. The removable recording medium 921 may be a CompactFlash (CF; registered trademark), a flash memory, an SD memory card (Secure Digital Memory Card), or the like. Alternatively, the removable recording medium 921 may be, for example, an IC card (Integrated Circuit Card) equipped with a non-contact IC chip or an electronic device.

The connection port 917 is a port for allowing devices to directly connect to the arithmetic processing apparatus 200. Examples of the connection port 917 include a USB (Universal Serial Bus) port, an IEEE1394 port, a SCSI (Small Computer System Interface) port, an RS-232C port, and the like. By the externally connected apparatus 923 connecting to this connection port 917, the arithmetic processing apparatus 200 directly obtains various data from the externally connected apparatus 923 and provides various data to the externally connected apparatus 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the arithmetic processing apparatus 200 according to an embodiment of the present invention has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

CONCLUSION

As described above, in a shape inspection apparatus and a shape inspection method for a metallic body according to an embodiment of the present invention, wavelengths of illumination light sources used for shape inspection are selected appropriately, so that the surface shape of a metallic body can be inspected accurately. Moreover, in a shape inspection apparatus and a shape inspection method for a metallic body according to an embodiment of the present invention, information for inspection can be obtained for each pixel of a captured image captured by a line sensor camera, which enables shape inspection with very high density. Furthermore, in a shape inspection apparatus and a shape inspection method for a metallic body according to an embodiment of the present invention, information for inspection can be calculated by simple arithmetic as described above, which enables shape inspection with very high speed.

EXAMPLES

Now, the shape inspection apparatus 10 according to the present invention will be described specifically with specific examples. Here, Examples described below are merely examples of a shape inspection apparatus and a shape inspection method according to the present invention, and a shape inspection apparatus and a shape inspection method according to the present invention are not limited to Examples described below.

Example 1

Figure 30:
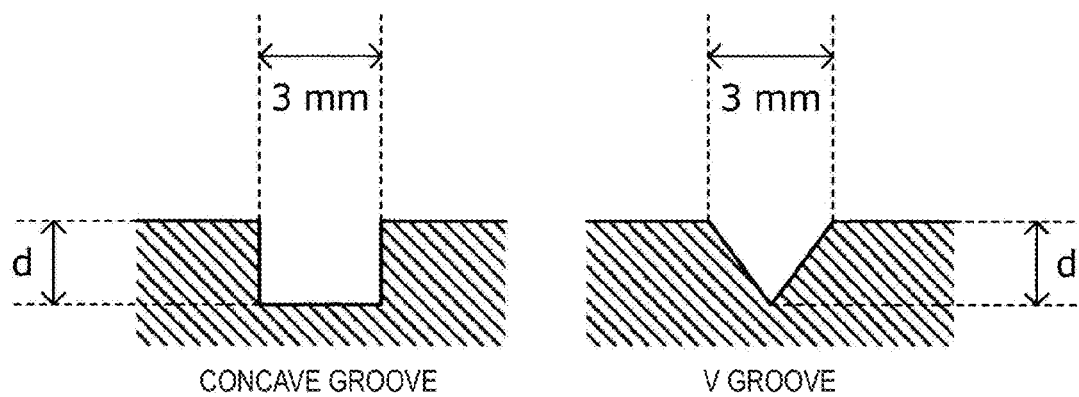
FIG. 30 is an explanatory diagram for explaining Example 1.

FIGS. 30 to 33 are explanatory diagrams for explaining Example 1. As illustrated in FIG. 30, in the present example, a steel plate was used as the metallic body S and two types of uneven shapes of concave grooves and V grooves illustrated in FIG. 30 were intentionally formed on the surface of the steel plate, and detection of these two types of uneven shapes was tested. Here, widths of the concave grooves and the V grooves were 3 mm, and depths d of the grooves were of four types, 50 μm, 100 μm, 200 μm, and 300 μm. In the steel plate, the V grooves were formed in the right half in the width direction of the steel plate, and the concave grooves were formed in the left half in the width direction. Furthermore, in the steel plate, grooves with four types of depths were formed in the longitudinal direction of the steel plate.

As the shape inspection apparatus 10 according to the present invention, the shape inspection apparatus 10 including the measurement apparatus 100 illustrated in FIGS. 2A and 2B was used. In the present example, blue light with a peak wavelength of 460 nm was used as the first illumination light, and green light with a peak wavelength of 530 nm was used as the second illumination light. The color line sensor camera 101 was installed perpendicularly to the surface of the steel plate, and $\theta_1$ and $\theta_2$ illustrated in FIG. 2A were each set to 45 degrees. The color line sensor camera 101 used in the present example had a resolution of 0.125 mm.

Using the shape inspection apparatus 10 as described above, a process of detecting the uneven shapes using the formula 113 was performed. Here, values decided appropriately in advance were used as the correction constant in the formula 113 and a conversion coefficient for converting a luminance difference into an angle.

As a comparative example, the steel plate having the uneven shapes described above was inspected using a shape inspection apparatus by a light-section method, which is generally used, as disclosed in Patent Literature 1. Also in this light-section method, image capturing resolution was set to 0.125 mm, an installation angle of a laser linear light source was set to 45 degrees, and an installation angle of an area camera was set to 0 degrees.

Figure 31:
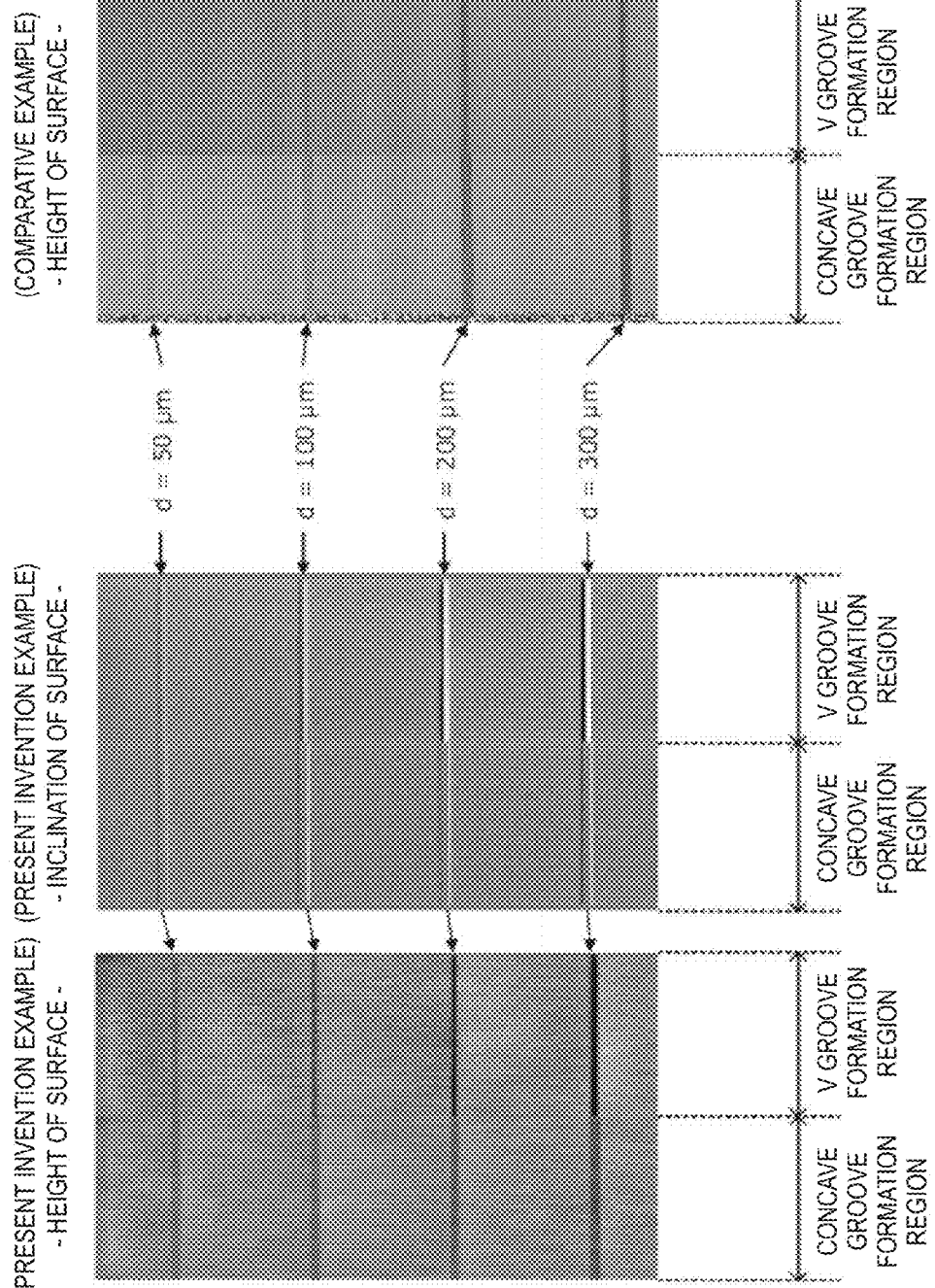
FIG. 31 is an explanatory diagram for explaining Example 1.
Figure 32:
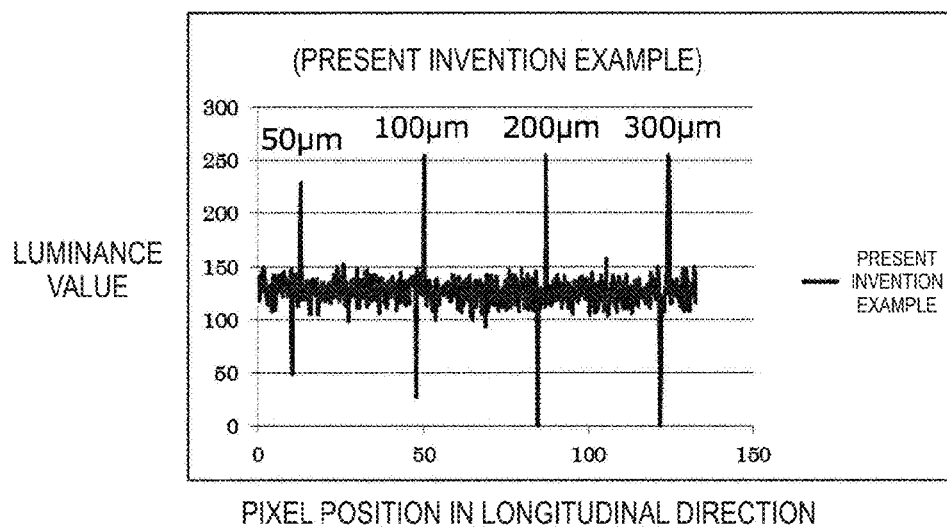
FIG. 32 is an explanatory diagram for explaining Example 1.
Figure 33:
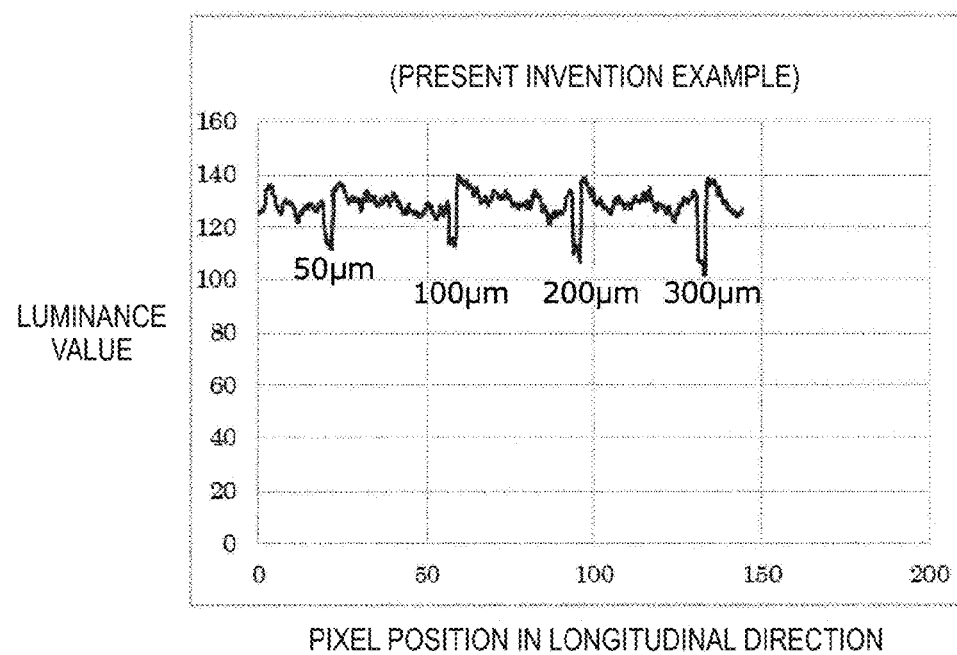
FIG. 33 is an explanatory diagram for explaining Example 1.

FIGS. 31 to 33 show the obtained results. The drawings on the right side and the left side in FIG. 31 show height images obtained by setting a height of 0 mm to 128 and making a range of −400 μm to 400 μm correspond to 8-bit images of 0 to 255, and the left-right direction of the drawing corresponds to the width direction of the steel plate and the up-down direction of the drawing corresponds to the longitudinal direction of the steel plate. The drawing at the center in FIG. 31 is an inclination image obtained by making inclinations of −10 degrees to 10 degrees correspond to 8-bit images of 0 to 255. According to the inclination calculation results in the shape inspection apparatus 10 according to an embodiment of the present invention, which are shown at the center of FIG. 31, contrast of the boundary between the groove portion and the normal portion is clear for each of the concave grooves and the V grooves, regardless of the depth of the groove. The image on the left side of FIG. 31 showing the height of the surface obtained by integrating the inclination also exhibits clear contrast. On the other hand, in the comparative example shown on the right side of FIG. 31, contrast of the boundary between the groove portion and the normal portion becomes unclear as the depth of the groove becomes shallower.

Figure 34:
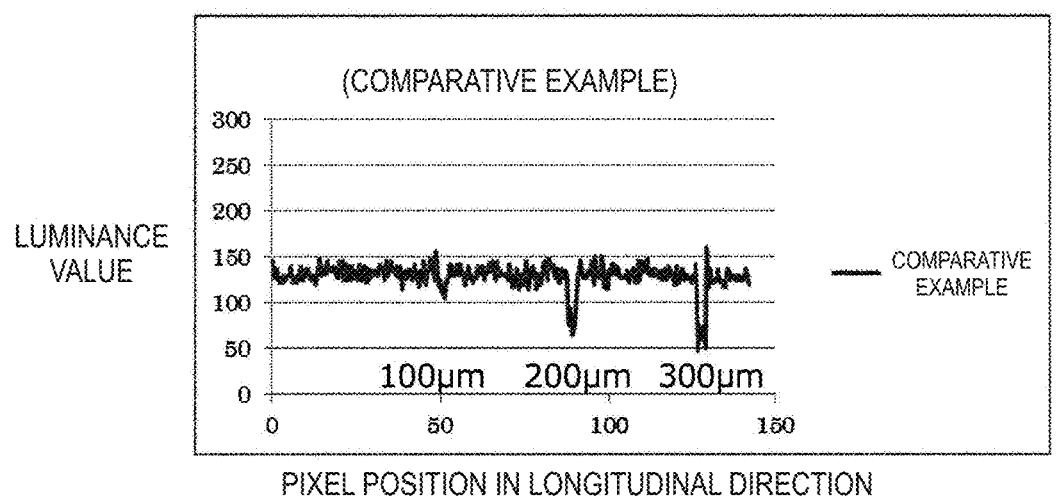
FIG. 34 is an explanatory diagram for explaining Example 1.

FIGS. 32 to 34 are graph diagrams showing cross-sectional profiles of a portion having the concave grooves of the height images shown in FIG. 31, and the vertical axis indicates a luminance value of the image and the horizontal axis indicates a position in the longitudinal direction of the image. FIG. 32 is a profile of the inclination of the surface in the results of the shape inspection apparatus 10 according to an embodiment of the present invention, and FIG. 33 is a profile (in other words, cross-sectional profile) of the height of the surface obtained by integrating the inclination of the surface shown in FIG. 32. FIG. 34 is a cross-sectional profile in the comparative example. FIGS. 32 and 33 reveal that in the shape inspection apparatus 10 according to an embodiment of the present invention, an edge is clearly detected at the boundary between the groove portion and the normal portion, regardless of the depth of the groove. On the other hand, in the results of the comparative example shown in FIG. 34, an edge at the boundary between the groove portion and the normal portion becomes unclear as the depth of the groove becomes shallower.

These results demonstrate that in the shape inspection apparatus 10 according to an embodiment of the present invention, a microscopic uneven shape of a groove depth of 50 μm can be detected favorably.

Now, a similar shape inspection apparatus 10 was used to perform a process on a flat hot-rolled steel plate having a roughness change caused on its surface by irregularity in scale occurrence but not having unevenness other than the surface roughness. Here, three different difference images were generated for the same hot-rolled steel plate by changing a combination of peak wavelengths of illumination light in the measurement apparatus 100.

The following three combinations of peak wavelengths of illumination light were used: (a) first illumination light=blue light with a peak wavelength of 460 nm, second illumination light=red light with a peak wavelength of 640 nm; (b) first illumination light=green light with a peak wavelength of 530 nm, second illumination light=red light with a peak wavelength of 640 nm; and (c) first illumination light=blue light with a peak wavelength of 460 nm, second illumination light=green light with a peak wavelength of 530 nm.

FIG. 35 shows the obtained results. Here, it was additionally confirmed that in the difference images shown in FIG. 35, root-mean-square roughness Rq of a dark-colored portion was 2.7 μm and root-mean-square roughness Rq of a light-colored portion was 2.1 μm.

As shown in FIG. 35, standard deviation of luminance values was 3.50 in the case (a), 3.09 in the case (b), and 2.06 in the case (c). An angle error was 1.6 degrees in the case (a), 1.4 degrees in the case (b), and 0.9 degrees in the case (c), being reflective of the situation of the standard deviation of luminance values.

In performing a shape inspection process using two types of colored light as illumination light, two types of colored light having peak wavelengths as much different as possible are ordinarily likely to be selected, as in the case (a) for example, in order to prevent color mixing of two types of illumination light. However, the above results demonstrate that the case (b) with a peak wavelength difference smaller than that in the case (a) provides a better result than the case (a), and the case (c) with a peak wavelength difference of 90 nm or less provides an even better result than the case (b).

Figure 36:
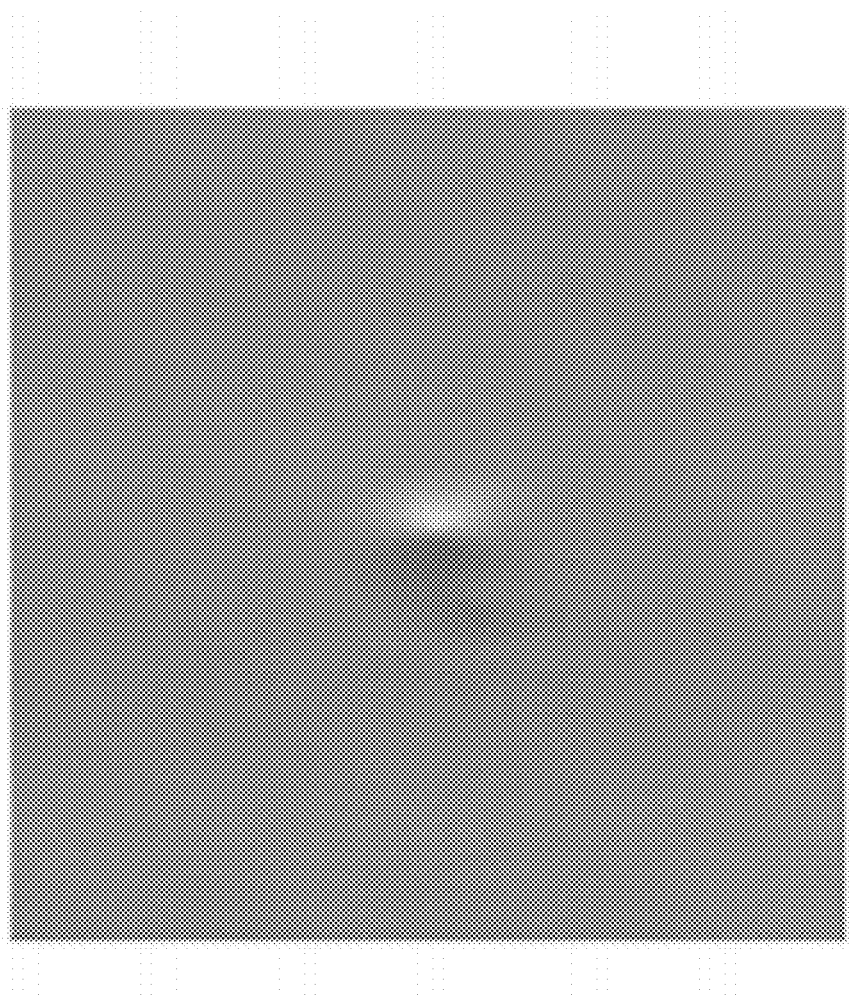
FIG. 36 is an explanatory diagram for explaining Example 1.

In addition, the third illumination light source 151 that emits red light with a peak wavelength of 640 nm was installed at a position in the vicinity of a regular reflection position of the measurement apparatus 100 ($\theta_3$=5 degrees in FIG. 21) as described above, and a convex portion with an amount of unevenness of 10 μm and a diameter of 3 mm present on a steel plate was observed; FIG. 36 shows the observation result. FIG. 36 reveals that even a microscopic shape of an amount of unevenness of 10 μm can be detected by installing the third illumination light source 151 in the vicinity of the regular reflection position and measuring regular reflection from the steel plate.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST

10 shape inspection apparatus
100 measurement apparatus
101 color line sensor camera
103 first illumination light source
105 second illumination light source
151 third illumination light source
200 arithmetic processing apparatus
201 data acquisition unit
203 measurement control unit
205 data processing unit
207 display control unit
209 storage unit
221 difference data generation unit
223, 251 inclination calculation unit
225 height calculation unit
227 result output unit

The invention claimed is:

1. A shape inspection apparatus for a metallic body, comprising:
   a measurement apparatus configured to irradiate a metallic body with at least two illumination light beams, and measure reflected light of the two illumination light beams from the metallic body separately; and
   an arithmetic processing apparatus having processing circuitry configured to calculate information used for shape inspection of the metallic body on the basis of measurement results of luminance values of the reflected light obtained by the measurement apparatus,
   wherein the measurement apparatus includes
      a first illumination light source and a second illumination light source configured to irradiate the metallic body with strip-shaped illumination light having mutually different peak wavelengths, and
      a color line sensor camera configured to measure reflected light of first illumination light emitted from the first illumination light source and reflected light of second illumination light emitted from the second illumination light source, separately,
   the first illumination light source and the second illumination light source are provided in a manner that an angle formed by a direction of regular reflection of an optical axis of the color line sensor camera at a surface of the metallic body and an optical axis of the first illumination light source is substantially equal to an angle formed by the regular reflection direction and an optical axis of the second illumination light source,
   a wavelength difference between a peak wavelength of the first illumination light and a peak wavelength of the second illumination light is equal to or more than 5 nm and equal to or less than 90 nm, and
   the arithmetic processing apparatus calculates an inclination of the surface of the metallic body as the information by using a difference between a luminance value of the reflected light of the first illumination light and a luminance value of the reflected light of the second illumination light.

2. The shape inspection apparatus for a metallic body according to claim 1, wherein a surface temperature of the metallic body is 570° C. or lower.

3. The shape inspection apparatus for a metallic body according to claim 1,
   wherein an angle formed by the optical axis of the color line sensor camera and a normal direction to the surface of the metallic body is 5 degrees or less, and
   the angle formed by the regular reflection direction and the optical axis of the first illumination light source and the angle formed by the regular reflection direction and the optical axis of the second illumination light source are each 30 degrees or more.

4. The shape inspection apparatus for a metallic body according to claim 1, wherein the peak wavelength of the first illumination light is 450 nm or more, and the peak wavelength of the second illumination light is 540 nm or less.

5. The shape inspection apparatus for a metallic body according to claim 1,
   wherein the measurement apparatus further includes, in the vicinity of the regular reflection direction, a third illumination light source capable of emitting third illumination light having a peak wavelength that differs from the peak wavelengths of the first illumination light and the second illumination light by 5 nm or more,
   the color line sensor camera further measures reflected light from the metallic body of the third illumination light, and
   the arithmetic processing apparatus calculates the inclination of the surface of the metallic body by using the difference and a luminance value of the reflected light of the third illumination light.

6. The shape inspection apparatus for a metallic body according to claim 5, wherein the peak wavelength of the third illumination light is equal to or more than 600 nm and equal to or less than 700 nm.

7. The shape inspection apparatus for a metallic body according to claim 1,
   wherein the difference is corrected in advance in a manner that when a metallic body with a flat surface is measured, a difference in luminance value between the two reflected light beams from the metallic body with a flat surface is zero, and
   the arithmetic processing apparatus specifies a direction of the inclination on the basis of a sign of the difference and specifies a magnitude of the inclination on the basis of an absolute value of the difference.

8. The shape inspection apparatus for a metallic body according to claim 1, wherein the arithmetic processing apparatus further calculates a height of the surface of the metallic body as the information by integrating the calculated inclination of the surface of the metallic body along a relative movement direction of the color line sensor camera and the metallic body.

9. The shape inspection apparatus for a metallic body according to claim 1, wherein the arithmetic processing apparatus inspects a shape of the metallic body by comparing the calculated inclination of the surface of the metallic body with a predetermined threshold value.

10. A shape inspection method for a metallic body, comprising:
irradiating a metallic body with at least first illumination light and second illumination light, and measuring reflected light of the illumination light from the metallic body separately, by a measurement apparatus including a first illumination light source and a second illumination light source configured to irradiate the metallic body with strip-shaped illumination light having mutually different peak wavelengths, and a color line sensor camera configured to measure reflected light of the first illumination light emitted from the first illumination light source and reflected light of the second illumination light emitted from the second illumination light source, separately, wherein the first illumination light source and the second illumination light source are provided in a manner that an angle formed by a direction of regular reflection of an optical axis of the color line sensor camera at a surface of the metallic body and an optical axis of the first illumination light source is substantially equal to an angle formed by the regular reflection direction and an optical axis of the second illumination light source, and a wavelength difference between a peak wavelength of the first illumination light and a peak wavelength of the second illumination light is equal to or more than 5 nm and equal to or less than 90 nm; and
calculating, by an arithmetic processing apparatus having processing circuitry configured to calculate information for shape inspection of the metallic body on the basis of measurement results of luminance values of the reflected light obtained by the measurement apparatus, an inclination of the surface of the metallic body as the information by using a difference between a luminance value of the reflected light of the first illumination light and a luminance value of the reflected light of the second illumination light.

11. The shape inspection method for a metallic body according to claim 10, wherein a surface temperature of the metallic body is 570° C. or lower.

12. The shape inspection method for a metallic body according to claim 10,
wherein an angle formed by the optical axis of the color line sensor camera and a normal direction to the surface of the metallic body is set to 5 degrees or less, and
the angle formed by the regular reflection direction and the optical axis of the first illumination light source and the angle formed by the regular reflection direction and the optical axis of the second illumination light source are each set to 30 degrees or more.

13. The shape inspection method for a metallic body according to claim 10, wherein the peak wavelength of the first illumination light is set to 450 nm or more, and the peak wavelength of the second illumination light is set to 540 nm or less.

14. The shape inspection method for a metallic body according to claim 10,
wherein the measurement apparatus further includes, in the vicinity of the regular reflection direction, a third illumination light source capable of emitting third illumination light having a peak wavelength that differs from the peak wavelengths of the first illumination light and the second illumination light by 5 nm or more, and the color line sensor camera further measures reflected light from the metallic body of the third illumination light, and
in a process of calculating the inclination of the surface in the arithmetic processing apparatus, the inclination of the surface of the metallic body is calculated by using the difference and a luminance value of the reflected light of the third illumination light.

15. The shape inspection method for a metallic body according to claim 14, wherein the peak wavelength of the third illumination light is set to equal to or more than 600 nm and equal to or less than 700 nm.

16. The shape inspection method for a metallic body according to claim 10,
wherein the difference is corrected in advance in a manner that when a metallic body with a flat surface is measured, a difference in luminance value between the two reflected light beams from the metallic body with a flat surface is zero, and
in a process of calculating the inclination of the surface in the arithmetic processing apparatus, a direction of the inclination is specified on the basis of a sign of the difference and a magnitude of the inclination is specified on the basis of an absolute value of the difference.

17. The shape inspection method for a metallic body according to claim 10, wherein, by the arithmetic processing apparatus, a height of the surface of the metallic body is further calculated as the information by integrating the calculated inclination of the surface of the metallic body along a relative movement direction of the color line sensor camera and the metallic body.

18. The shape inspection method for a metallic body according to claim 10, wherein, by the arithmetic processing apparatus, a shape of the metallic body is inspected by comparing the calculated inclination of the surface of the metallic body with a predetermined threshold value.

* * * * *